United States Patent [19]
Watanabe et al.

[11] Patent Number: 5,736,522
[45] Date of Patent: Apr. 7, 1998

[54] ESCULETIN DERIVATIVES AND METHOD FOR MANUFACTURE THEREOF, USE THEREOF, AND PHARMACEUTICAL COMPOSITION

[75] Inventors: Koju Watanabe; Koichi Niimura, both of Saitama; Junko Miyagawa, Chiba, all of Japan

[73] Assignee: Kureha Chemical Industry Co., Ltd., Tokyo, Japan

[21] Appl. No.: 340,421

[22] Filed: Nov. 15, 1994

[30] Foreign Application Priority Data

Nov. 15, 1993 [JP] Japan ..................... 5-308779

[51] Int. Cl.$^6$ ..................... A61K 31/70; C07H 1/00; C07H 15/00
[52] U.S. Cl. ..................... 514/25; 536/8; 536/18.5; 536/18.6
[58] Field of Search ..................... 536/8, 18.5, 18.6; 514/25

[56] References Cited

U.S. PATENT DOCUMENTS

| | | | |
|---|---|---|---|
| 3,876,777 | 4/1975 | Horowitz et al. | 514/25 |
| 4,211,772 | 7/1980 | Fauran et al. | 424/180 |
| 4,238,483 | 12/1980 | Frazier | 514/25 |
| 4,616,007 | 10/1986 | Lang | 514/192 |
| 5,414,073 | 5/1995 | Okuyama et al. | 536/18.5 |

FOREIGN PATENT DOCUMENTS

| | | |
|---|---|---|
| A0614896 | 9/1994 | European Pat. Off. |
| A2112098 | 6/1972 | France |

OTHER PUBLICATIONS

Kuwajima, H. et al, Secoiridoid, Coumarin and Secoiridoid-–Coumarin Glucosides from *Fraxinus chinensis*, Phytochemistry, vol. 31, No. 4, pp. 1277–1280 (1992).

Gorecke, P. et al. The Synthesis of Esculin, Herba Polonica, vol. 17, No. 1&2, pp. 46–51 (1971).

Miyake, T. et al, Biosynthesis of Esculin Glucoside, Vitamins, vol. 45, No. 6, pp. 340–343 (1972).

Jassey, Y. et al, Comparaison de la Teneur en Phenolamides Des Graines dormantes Ou non Dormantes de Deux Lignees de Petunia, Physiol. Veg:, vol. 20, No. 4, 641–50 (1982).

Phytochemistry, vol. 29, 1990, pp. 3369–3371, M.A. Dubois et al. 'Palustroside, A Coumarin Glucoside Ester From Ledum Palustre'.

Chemical Abstracts, vol. 84, No. 15, 1976, Columbus, OH, US; Abstract No. 104899, I.P. Kovalev et al. 'Stereochemistry of Some Optically Active Coumarine Derivatives' p. 518; col. 1.

Chemical Abstracts, vol. 112, No. 9, 1990, Columbus, OH, US; Abstract No. 73766, G. Nonaka 'Tannins and Related Compounds' p. 474; col. R.

Database WPI Derwent Publications Ltd., London, GB: Abstract of An 71-16013s and JP-A-46 007 687 (Nihon Shinyaku KK), 1971.

Database WPI Derwent Publications Ltd., London, GB: Abstract of An 71-16012s and JP-A-46 007 686 (Nihon Shinyaku KK), 1971.

Chemical Abstracts, vol. 119, No. 5, 1993, Columbus Ohio, US; Abstract No. 45257, H. Zhao et al. Constituents of Roots of Chinonanthus Praecox'p. 541.

Chemical Abstracts, vol. 95, No. 24, 1981, Columbus, OH, US; Abstract No. 209451. H.Z. Ye et al. 'Study of the Antirheumatic Active Principle of Ding Gong–Teng'; p. 361; col. 1.

Chemical Abstracts, vol. 88, No. 9, 1978, Columbus, OH, US; Abstract No. 58458, N. Beuscher 'Effect of a Benzopyrone Preparation on Experimental Rheumatoid Illness' p. 42; col. R.

*Primary Examiner*—Elli Peselev
*Attorney, Agent, or Firm*—Sughrue, Mion, Zinn, Macpeak & Seas, PLLC

[57] ABSTRACT

A compound of the formula (I):

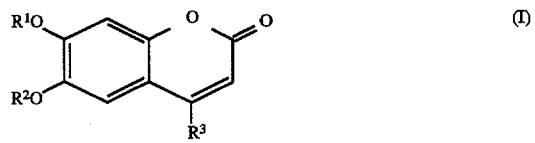

wherein $R^1$ and $R^2$ are, independently, a hydrogen atom, a monosaccharide residue, a protected monosaccharide residue, or a protecting group for hydroxyl group, but at least one of $R^1$ and $R^2$ is a monosaccharide residue or a protected monosaccharide residue, and $R^3$ is a hydrogen atom, a hydroxyl group, an alkyl group, an aryl group, or an aralkyl group, with the proviso that (1) when $R^1$ and $R^2$ are glucose residues at the same time, $R^3$ is not a hydrogen atom, (2) when $R^1$ is a hydrogen atom, an acetyl group or a benzyl group and $R^2$ is a glucose residue, an acetylated glucose residue, or acetalized glucose residue, $R^3$ is not a hydrogen atom, or (3) when $R^1$ is a glucose residue and $R^2$ is a hydrogen atom, $R^3$ is not a hydrogen atom or a salt thereof is disclosed.

8 Claims, 1 Drawing Sheet

ESCULETIN DERIVATIVES AND METHOD FOR MANUFACTURE THEREOF, USE THEREOF, AND PHARMACEUTICAL COMPOSITION

BACKGROUND OF THE INVENTION

1. Field of the Invention

The present invention relates to esculetin derivatives and a method for manufacture thereof, a use thereof, and a pharmaceutical composition, more particularly an agent for protecting cartilage, i.e., a chondroprotective agent. The esculetin derivatives of the present invention can be administered effectively, for example, to mammals suffering from arthropathy.

2. Description of the Related Art

There are various types of arthropathy, for example, rheumatoid arthritis, rheumatic fever, and osteoarthritis Many people particularly suffer from rheumatoid arthritis and osteoarthritis, and these diseases are considered the major types of arthropathy. There are congenital and secondary osteoarthritis, and further primary osteoarthritis caused by degeneration of the articular cartilage along with aging. Patients suffering from primary osteoarthritis have recently been increasing along with the increase in the population of the aged. Therefore, development of medicines for its treatment having new actions and functions is desired, Although there are considerable differences of the causes and conditions between rheumatoid arthritis and osteoarthritis, the articular function becomes eventually obstructed by the destruction of the cartilage in both of rheumatoid arthritis and osteoarthritis.

The first choice of medicines for treatment of rheumatic diseases such as rheumatoid arthritis, rheumatic fever, systemic lupus erythematosus, or osteoarthritis are analgesic and anti-inflammatory agents, for example, aspirin or indomethacin. Further, gold compounds (for example, Shiosol), immunomodulators, steroids, or D-penicillamine are used as the medicine for treatment of rheumatoid arthritis.

The above conventional analgesic and anti-inflammatory agents, however, were not effective against the destruction of the articular cartilage, and in fact, sometimes exhibited adverse effect in the experiments using chondrocytes. Further, clinically, no function to suppress the destruction of articular cartilage was found in the above medicines for treatment of rheumatoid arthritis and osteoarthritis.

The articular cartilage is composed of chondrocytes and the cartilage matrix. The cartilage matrix has a three-dimensional structure which is formed by non-covarently binding the type II collagen, which is the fibrous protein produced by the chondrocytes, and the glycoprotein complex, proteoglycan, with hyaluronic acid to cause complicated entanglement. The matrix holds a large amount of water, which enables the normal articular functions to be maintained. The main polysaccharide constituting the proteoglycan is glycosaminoglycan (hereinafter sometimes referred to as "GAG"), which is composed of chondroitin sulfate and keratan sulfate.

The present inventors and a co-worker discovered that esculetin and 4-methylesculetin which are known compounds strongly suppress the reduction in the GAG in the matrix caused by stimulation of interleukin-1 or the like, and thus, are useful as chondroprotective agents.

SUMMARY OF THE INVENTION

The present inventors engaged in intensive research to develop novel compounds with a chondroprotective action, and as a result, discovered that an amount taken up into the cartilage matrix, i.e., affinity to the cartilage matrix may be improved by novel esculetin derivatives formed by binding esculetin or 4-alkylesculetin with monosaccharides having structures similar to those of the components contained in the cartilage matrix.

Accordingly, the object of the present invention is to provide novel esculetin derivatives by which an amount taken up into the cartilage matrix, i.e., affinity to the cartilage matrix may be improved.

Other object and advantages of the present invention will be apparent from the following description.

The present invention relates to an esculetin derivative of the formula (I):

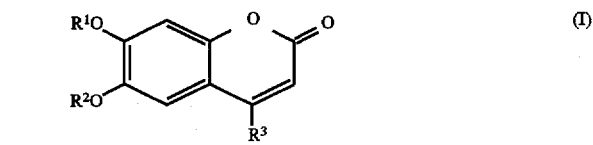

wherein $R^1$ and $R^2$ are, independently, a hydrogen atom, a monosaccharide residue, a protected monosaccharide residue, or a protecting group for hydroxyl group, but at least one of $R^1$ and $R^2$ is a monosaccharide residue or a protected monosaccharide residue, and $R^3$ is a hydrogen atom, a hydroxyl group, an alkyl group, an aryl group, or an aralkyl group, with the proviso that (1) when $R^1$ and $R^2$ are glucose residues at the same time, $R^3$ is not a hydrogen atom, (2) when $R^1$ is a hydrogen atom or a benzyl group and $R^2$ is a glucose residue, an acetylated glucose residue, or acetalized glucose residue, $R^3$ is not a hydrogen atom, or (3) when $R^1$ is a glucose residue and $R^2$ is a hydrogen atom, $R^3$ is not a hydrogen atom, or a salt thereof (hereinafter sometimes referred to as the present substance).

Further, the present invention relates to a method for manufacturing a compound of the formula (XV)

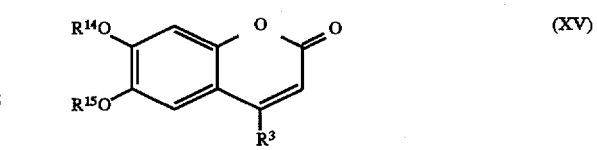

wherein $R^{14}$ and $R^{15}$ are independently a protected monosaccharide residue or a protecting group for hydroxyl group, but at least one of $R^{14}$ and $R^{15}$ is a protected monosaccharide residue, and $R^3$ is a hydrogen atom, a hydroxyl group, an alkyl group, an aryl group, or an aralkyl group, comprising reacting a compound of the formula (XVI)

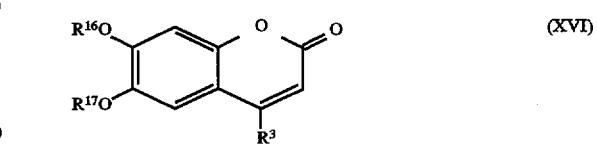

wherein $R^{16}$ and $R^{17}$ are independently a hydrogen atom, a protected monosaccharide residue, or a protecting group for hydroxyl group, but at least one of $R^{16}$ and $R^{17}$ is a hydrogen atom, and $R^3$ has the same meaning as above, and a compound of the formula (IV)

$$R^5\text{—}X \qquad (IV)$$

wherein $R^5$ is a protected monosaccharide residue and X is a halogen atom.

Further, the present invention relates to a method for manufacturing a compound of the formula (XIII):

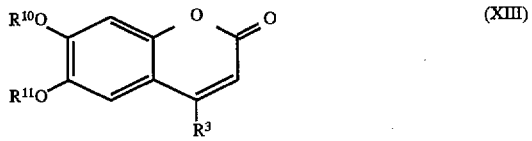

wherein one of $R^{10}$ and $R^{11}$ is a monosaccharide residue or a protected monosaccharide residue and the other is a hydrogen atom, and $R^3$ is a hydrogen atom, a hydroxyl group, alkyl group, aryl group, or aralkyl group, comprising hydrogenating a compound of the formula (XIV):

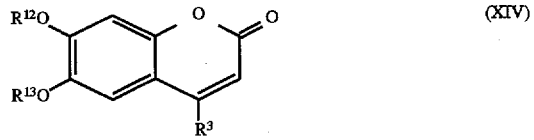

wherein one of $R^{12}$ and $R^{13}$ is a monosaccharide residue or a protected monosaccharide residue and the other is a protecting group for hydroxyl group, and $R^3$ has the same meaning as above.

Further, the present invention relates to a method for manufacturing a compound of a compound of the formula (XI):

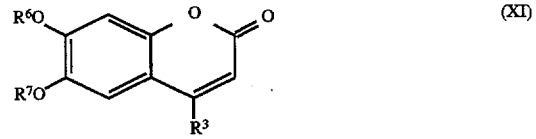

wherein $R^6$ and $R^7$ are independently a hydrogen atom, a monosaccharide residue, or a protecting group for hydroxyl group, but at least one of $R^6$ and $R^7$ is a monosaccharide residue, and $R^3$ is a hydrogen atom, a hydroxyl group, alkyl group, aryl group, or aralkyl group, comprising removing one or more protecting groups in a protected monosaccharide residue in a compound of the formula (XII):

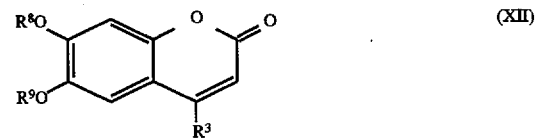

wherein $R^8$ and $R^9$ are independently a hydrogen atom, a protected monosaccharide residue, or a protecting group for hydroxyl group, but at least one of $R^8$ and $R^9$ is a protected monosaccharide residue, and $R^3$ has the same meaning as above.

Further, the present invention relates to a pharmaceutical composition comprising the esculetin derivative of the formula (I) or a pharmaceutically acceptable salt thereof, and a pharmaceutically acceptable carrier.

DESCRIPTION OF THE PREFERRED EMBODIMENTS

Figure 1:
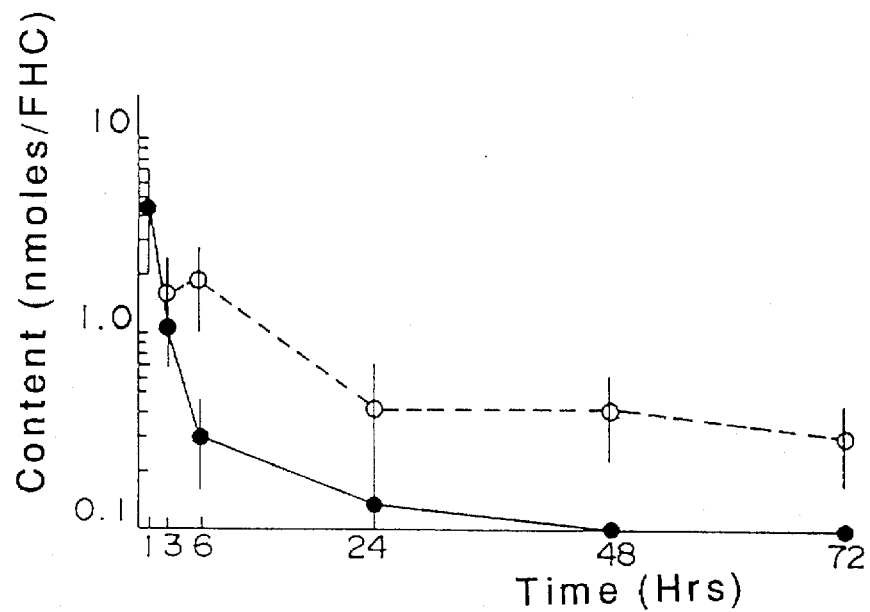
FIG. 1 is a graph showing the amounts of the compound of the present invention and esculetin taken up in the femoral head cartilage (FHC) in a mouse FHC model, as disclosed in Example 28(2)

The present invention will be described in detail hereinafter.

The term "monosaccharide residue" used herein means a group formed by removing 1-hydroxyl group from a monosaccharide compound.

These monosaccharide compounds are not only compounds of $(CH_2O)n$ (where n is an integer of 3 or more), but also include the derivatives thereof, for example, deoxy sugars, aminosugars, saccharic acids, sugar alcohols, or the like; esters, such as sulfates or phosphates; salts of these esters; ethers such as methylether; and salts of amino sugars, or saccharic acids, or the like. Concrete examples of the monosaccharides are mentioned in Takashi Mizuno and Kazutoshi Nishizawa ed., "Zukai Tohsitukagaku Binran (Illustrated Carbohydrate Chemistry Handbook)", published by Kyoritsu Shuppan Co., Japan (1971).

Preferred monosaccharides are pentoses and hexoses. Preferred examples of pentoses are arabinose, xylose, ribose, and deoxyribose. Preferred examples of hexoses are mannose, allose, altrose, talose, glucose, galactose, idose, gulose, fructose, rhamnose, fucose, glucosamine, N-acylglucosamine, galactosamine, N-acylgalactosamine, N-acylmuramic acid, glucuronic acid, gulonic acid, iduronic acid, ascorbic acid, mannitol, and sorbitol. Further, possible esters such as sulfates or phosphates, and salts of these monosaccharides are also included.

The more preferred monosaccharides are mannose, glucose, galactose, fructose, rhamnose, fucose, glucosamine, N-acylglucosamine, galactosamine, N-acylgalactosamine, and glucuronic acid. Further, possible esters such as sulfates or phosphates, and salts of these monosaccharides are also included.

The acyl group of the N-acylsaccharide is preferably an aliphatic acyl group of 2 to 20 carbon atoms, more preferably an alkanoyl group of 2 to 5 carbon atoms, still more preferably an acetyl group.

The term "protected monosaccharide residue" used herein is a group of a monosaccharide wherein at least one of hydroxyl groups is protected. The protecting group may be any groups commonly used as a protecting group for a hydroxyl group in saccharides, for example, a protecting group formed by acylation, acetalization, sulfuric esterification, or phosphoric esterification, preferably an acyl group. The acyl group used as a protecting group of a hydroxyl group in a monosaccharide residue is preferably an aliphatic acyl group of 2 to 20 carbon atoms, more preferably an alkanoyl group of 2 to 10 carbon atoms, still more preferably an acetyl group or pivaloyl group. Preferred examples of the protected monosaccharide residue are the above-mentioned pentose or hexose residues wherein one to all of hydroxyl groups are protected by the above acyl groups. Particularly preferred are monosaccharide residues wherein all hydroxyl groups are protected by acetyl groups or wherein one hydroxyl group is protected by a pivaloyl group.

Further, the protected monosaccharide residue may be a group of the above-mentioned monosaccharide (in particular the above-mentioned pentose or hexose) having two or four hydroxyl groups cyclised by forming acetal with one or two aldehyde compounds of the formula:

$R^{18}CHO$ wherein $R^{18}$ is a hydrogen atom, an alkyl group of 1 to 6 carbon atoms, a phenyl group, or a substituted phenyl, and 1 to 5 substituents on the substituted phenyl group is a hydroxyl group, an alkoxyl group of 1 to 6 carbon atoms, and/or an alkyl group of 1 to 6 carbon atoms. A monosaccharide residue (in particular the above-mentioned pentose or hexose residue) wherein 4-hydroxyl group and 6-hydroxyl group are acetalized with formalin, benzaldehyde, or methoxybenzaldehyde to form a 6-membered ring is particularly preferable. More particularly, 4- and 6-hydroxyl groups are protected by a methylidene group when $R^{18}$ is a hydrogen atom, by an alkyl-substituted methylidene group when $R^{18}$ is an alkyl group of 1 to 6 carbon atoms, by a benzylidene group when $R^{18}$ is a phenyl group, and by a substituted benzylidene group when $R^{18}$ is a substituted phenyl.

When one or more hydroxyl groups of the monosaccharide residue (in particular the above-mentioned pentose or hexose residue) are protected by one or more acyl, methylidene, or benzylidene groups, fat-solubility of the esculetin derivatives of the present invention increases and the bioavailability is improved.

Further, the protected monosaccharide residue may be a group of the above-mentioned monosaccharide residues (in particular the above-mentioned pentose or hexose residues) wherein one to all of the hydroxyl groups are sulfated or phosphated. Salts of alkali metals (for example lithium, sodium, or potassium) or ammonium salts of the esters are also included. When one or more hydroxyl groups of the monosaccharide residue (in particular the above-mentioned pentose or hexose residues) are protected by sulfate esters or phosphate esters, the water-solubility of the esculetin derivatives of the present invention is increased and the concentration in the blood can be increased.

The monosaccharide and protected monosaccharide residues in the esculetin derivatives of the present invention may have D-configuration or L-configuration, and pyranose structure or furanose structure.

In the esculetin derivatives of the present invention, the esculetin or 4-substituted esculetin moiety is bonded with the monosaccharide or protected monosaccharide residues by a glycoside bond. The configuration of 1-position of the glycoside may be an α-anomer or a β-anomer.

The protecting group for hydroxyl group of $R^1$ or $R^2$ in the formula (I) is not particularly limited insofar as it is a group which can be removed by hydrogenolysis. For example, it may be a benzyloxycarbonyl group or preferably a benzyl group.

The alkyl group of $R^3$ of the formula (I) is preferably an aliphatic alkyl group, more preferably a lower alkyl group of 1 to 4 carbon atoms, such as, methyl, ethyl, n-propyl, isopropyl, n-butyl, isobutyl, s-butyl, or t-butyl group. Methyl group or ethyl group is particularly preferable.

The aryl group of $R^3$ in the formula (I) is preferably an aryl group of 6 to 12 carbon atoms, for example, phenyl, naphthyl, or biphenyl group. These aryl groups may be substituted by one or more lower alkyl groups, for example, a lower alkyl group of 1 to 4 carbon atoms, a halogen atom, and/or a hydroxyl group.

Further, the aralkyl group of $R^3$ of the formula (I) is preferably a lower alkyl group of 1 to 4 carbon atoms substituted with an aryl group of 6 to 12 carbon atoms, for example, benzyl, phenylethyl, phenylpropyl, or phenylbutyl group. The aryl moiety of the aralkyl group may also be substituted by one or more substituent groups, for example, a lower alkyl group of 1 to 4 carbon atoms, a halogen atom, and/or a hydroxyl group.

The esculetin derivatives of the present invention wherein the 4-substituent group $R^3$ is a hydrogen atom is an esculetin glycoside. When $R^3$ is an alkyl group, aryl group, or aralkyl group, the esculetin derivative is a 4-alkylesculetin glycoside, 4-arylesculetin glycoside, or 4-aralkylesculetin glycoside.

In the esculetin derivatives of the present invention, at least one of $R^1$ and $R^2$ must be a monosaccharide residue or a protected monosaccharide residue. In other words, the esculetin derivatives of the present invention may be a monoglycoside wherein only one of the groups is a monosaccharide residue or a protected monosaccharide residue or a diglycoside wherein both of the groups are monosaccharide residues or protected monosaccharide residues.

The salts of the esculetin derivatives of the present invention are formed at the 6- or 7-hydroxyl groups, in a sulfurate ester or phosphate ester of the sugar, at carboxylic groups of saccharic acid such as uronic acid, or at amino groups of amino sugar.

The pharmaceutically acceptable salts may be salts with inorganic or organic acids, or salts with inorganic or organic bases. As the acid addition salts, there may be mentioned, for example, salts of hydrochlorides, sulfates, methanesulfonates, or p-toluenesulfonates and, further, salts of dicarboxylic acids, such as oxalic, malonic, succinic, maleic, or fumaric acid, or monocarboxylic acids, such as acetic, propionic, or lactic acid. Further, the inorganic bases suited for formation of the salts of the present substance are, for example, hydroxides, carbonates or bicarbonates of ammonia, potassium, sodium, lithium, calcium, magnesium, or aluminum. As the organic bases, there may be mentioned, for example, mono-, di-, or tri-alkylamine salts, such as methylamine, dimethylamine, triethylamine, mono-, di-, and tri-hydroxyalkylamine salts, guanidine salts, N-methylglucosamine salts, amino acid salts, and so on.

Esculin, esculin glucoside, cichoriin, esculin-2',3',4',6'-tetraacetate, 7-benzyloxy-6-(β-D-glucopyranosyloxy) coumarin and tetraacetate thereof, and 6-[4,6-O-[(3,4-dihydroxyphenyl)-methylene]-β-D-glucopyranosyloxy]-7-hydroxylcoumarin are known compounds, and so are excluded from the esculetin derivatives of the present invention. That is, in the above formula (I), the cases where (1) $R^1$ and $R^2$ are both glucose residues at the same time, and $R^3$ is a hydrogen atom, (2) $R^1$ is a hydrogen atom or benzyl group and $R^2$ is a glucose residue, an acetylated glucose residue, or acetalized glucose residue, and $R^3$ is a hydrogen atom, or (3) $R^1$ is a glucose residue and $R^2$ is a hydrogen atom, and $R^3$ is a hydrogen atom, are excluded from the esculetin derivatives of the present invention. It was not known that the esculetin derivatives of the above cases (1) to (4) exhibit chondroprotective actions.

The esculetin derivatives of the present invention can be prepared by the following processes. Typical examples of the manufacturing processes will be explained in two cases of a monoglycoside and a diglycoside.

(1) Preparation of monoglycoside

The basic reaction scheme (I) for manufacturing an esculetin-6-glycoside compound or 4-substituted-esculetin-6-glycoside compound is as follows:

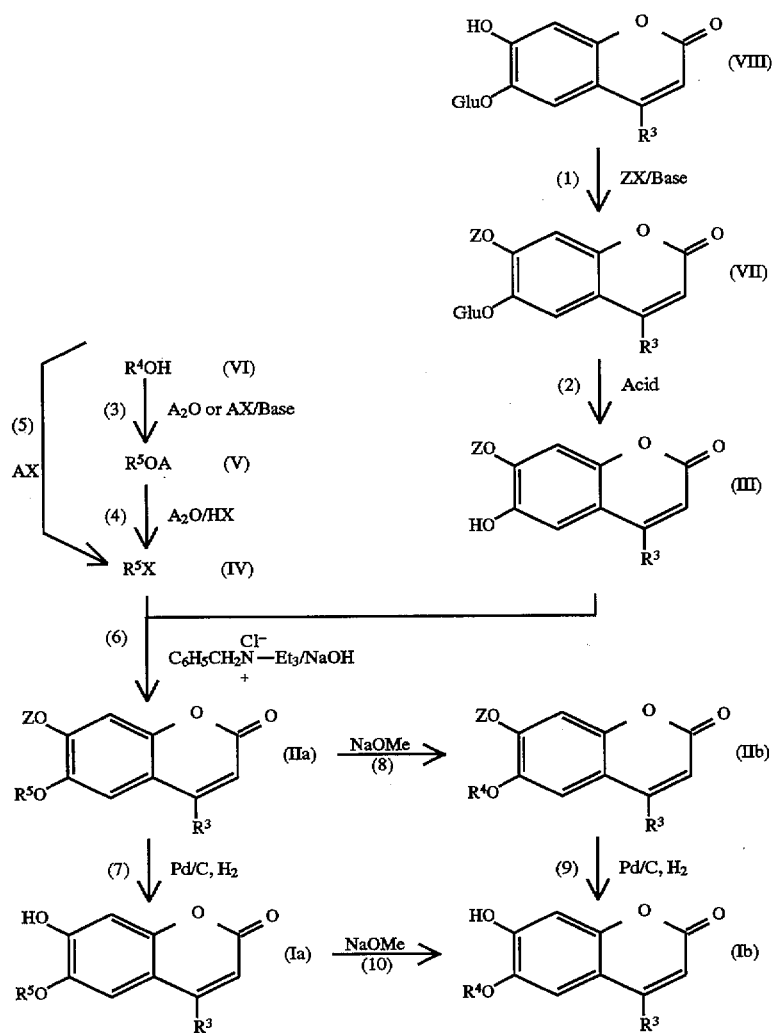

The steps (1) to (10) in the above reaction scheme (I) will be explained hereinafter as steps 1 to 10.

It is noted that the above-mentioned reaction scheme (I) may be converted to the basic reaction scheme of the case of manufacturing the esculetin-7-glycoside compound or 4-substituted esculetin-7-glycoside compound by replacing the 6-substituent groups of the compounds in the reaction scheme (I) with 7-substituent groups. Therefore, the following explanation will be made as if the case of manufacturing an esculetin-7-glycoside compound or 4-substituted esculetin-7-glycoside compound is included in the above reaction scheme (I).

In the reaction scheme (I), first, the compound (III) having a protected 7-hydroxyl group (or a protected 6-hydroxyl group) is prepared, When $R^3$ is a hydrogen atom, the compound (III) may be obtained by protecting the hydroxyl group with a protecting group (step 1) in the starting compound, namely, the esculetin compound having 6-hydroxy group protected with glucose residue (that is, 7-hydroxyl-6-glucosyloxycoumarin) (VIII), or the cichoriin compound having 7-hydroxy group protected with glucose residue (that is, 6-hydroxyl-7-glucosyloxycoumarin), and then, performing hydrolysis (step 2). Esculin and cichoriin are naturally occurring materials and available as reagents. Further, it is possible to use esculetin as a starting material and perform a step similar to step 1 as mentioned below so as to prepare esculetin compound (III) wherein one of two hydroxyl groups is protected.

When $R^3$ is an alkyl group, a 4-substituted esculetin compound (III) wherein one of two hydroxyl groups is protected is prepared from a starting material of 4-substituted esculetins, such as, 4-methylesculetin, 4-ethylesculetin, 4-n-propylesculetin, 4-i-propylesculetin, 4-n-butylesculetin, 4-i-butylesculetin, 4-t-butylesculetin. When $R^3$ is an aryl or aralkyl group, 4-arylesculetin or 4-aralkylesculetin compound (III) is similarly prepared.

Of the 4-alkylesculetin compounds, 4-methylesculetin is commercially available as a reagent from, for example, Tokyo Kasei Kogyo K.K. Further, the 4-substituted esculetin compound can be prepared in accordance with the Kostanecki-Robinson reaction (T. C. Chadha, H. S. Mahal, J. Chem. Soc., 1933, p. 1459) by reacting the compound of the formula (IX):

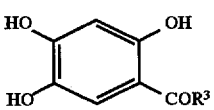

wherein $R^3$ is an alkyl group, aryl group, a hydroxyl group, or aralkyl group, acetic anhydride, and sodium acetate. If the compound of the formula (IX) wherein the $R^3$ is a hydrogen atom, it is possible to prepare esculetin by a similar reaction.

The resulting 4-substituted esculetin compound is used as a starting material to prepare a 4-substituted esculetin compound (III) wherein one of two hydroxyl groups is protected by a reaction step similar to step 1 described below. For example, it is possible to easily obtain a 4-substituted esculetin compound having 6- or 7-hydroxyl group protected with a benzyl group by reacting benzyl chloride therewith in an alcohol solution in the presence of a basic catalyst such as potassium carbonate. Protected esculetin can be obtained in the same manner.

(1) Step 1

This step [(1) in reaction scheme (I)] is the reaction to obtain the compound (VII) by introducing a protecting group at 7-hydroxyl group of the esculin compound (VIII) (wherein Glu indicates a glucose residue). When cichoriin is used as a starting material, it is possible to obtain a compound having the 6- and 7-substituent groups corresponding to 7- and 6-substituent groups in the above compound, respectively. In this reaction step, the compound ZX comprising the protecting group Z of the hydroxyl group and the halogen atom X (for example, benzyl chloride or benzyloxycarbonyl chloride) and the compound (VIII), for example, esculin or cichoriin, are reacted in an organic solution in the presence of a base at 4° to 80° C. for 0.5 to 48 hours to obtain the compound (VII). This reaction is preferably performed in the presence of a chelating agent, for example, 18-crown-6-ether and potassium iodide. As the protecting group Z, a group which can be removed by hydrolysis, for example, the benzyl group, benzyloxycarbonyl group, or the like is used. Examples of the organic solvent are dimethylformamide, methanol, or ethanol, and examples of the base are sodium or potassium carbonate.

(2) Step 2

This step [(2) in reaction scheme (I)] is the reaction for hydrolyzing the esculetin compound (VII) having the protected 7-hydroxyl group to obtain an esculetin compound (III) having a protected 7-hydroxyl group. Similarly, it is possible to hydrolyze the cichoriin compound having the protected 6-hydroxyl group to obtain an esculetin derivative having a protected 6-hydroxyl group. The mixture of an acid aqueous solution such as a hydrohalogenic acid and an organic solvent such as alcohol and the esculetin compound (VII) having the protected 7-hydroxyl group or cichoriin compound having the protected 6-hydroxyl group is reacted at 40° to 120° C., preferably under heating and reflux, for 0.5 to 10 hours to obtain the compound (III).

(3) Step 3

This step [(3) in reaction scheme (I)] is the reaction for protecting (for example, acylating) the hydroxyl group of the monosaccharide. For example, the monosaccharide of the formula:

R⁴OH　(VI)

wherein R⁴ is a monosaccharide residue, and acid anhydride of the formula:

A₂O wherein A is an acyl group, or halogenated acyl of the formula:

AX wherein A is an acyl group and X is a halogen atom, are reacted in the presence of a base, such as pyridine or sodium hydroxide, and, if necessary, in a suitable solvent, for example, chloroform, methanol, water, or the like, to obtain the acylated monosaccharide of the formula:

R⁵OA　(V)

wherein R⁵ is an acylated monosaccharide residue and A has the same meaning as above. The reaction temperature is generally −20° C. to +50° C., preferably room temperature. The reaction time is generally 1 hour to 2 days.

(4) Step 4

This step [(4) in reaction scheme (I)] is the reaction for substituting a halogen atom for the 1-acyoxyl group of the acylated monosaccharide. For example, gaseous halogenated hydrogen of the formula

HX wherein X indicates a halogen atom, is dissolved in carboxylic anhydride compound of the formula

A₂O wherein A is an acyl group, such as acetic anhydride, and then, the acylated monosaccharide compound of the formula

R⁵OA　(V)

wherein R⁵ is an acylated monosaccharide residue and A has the same meaning as above, is reacted therewith to obtain the acylated monosaccharide compound of the formula

R⁵X　(IV)

wherein R⁵ and X have the same meanings as above, having the 1-acyloxyl group substituted with a halogen atom. The reaction temperature is generally −20° C. to +50° C., preferably room temperature. The reaction time is generally 0.1 hour to 10 days.

(5) Step 5

This step [(5) in reaction scheme (I)] is the reaction for obtaining the above-mentioned compound R⁵X (IV) by one step reaction from the above-mentioned monosaccharide compound R⁴OH (VI). For example, a halogenated acyl (AX) is reacted with the monosaccharide compound (VI) to obtain the compound (IV). The reaction temperature is generally 4° C. to 80° C. The reaction time is generally 0.5 hours to 2 days.

In the above steps 1, 3, 4, and 5, the halogen atom X is not necessarily the same atom.

(6) Step 6

This step [(6) in reaction scheme (I)] is the reaction for introducing the protected (for example, acylated) monosaccharide residue to the 6- (or 7-) unprotected hydroxyl group in the esculetin compound (III) having the protected 7- (or 6-) hydroxyl group. For example, the compound (III) is reacted with the monosaccharide derivative (IV) in an organic solvent containing alkali aqueous solution, such as a caustic alkali aqueous solution/acetone solution at 4° to 80° C to obtain the compound (IIa). Alternatively, the compound (III) and monosaccharide derivative (IV) are dissolved in an organic solvent such as chloroform or acetonitrile. And then a halogenated ammonium salt (phase transfer catalyst) having an organic group dissolved in a caustic alkali aqueous solution or triethylamine or the like (basic catalyst) is added dropwise to the above solution at 4° to 50° C. Then, a reaction is performed at 4° to 80° C. for 0.5 hours to 10 days to obtain the compound (IIa). An example of the caustic alkali aqueous solution is sodium hydroxide aqueous solution, and an example of the halogenated ammonium salt having an organic group is benzyltriethylammonium chloride. The phase transfer catalyst means a reagent which can freely move through the aqueous phase and organic phase, for example, benzyltriethylammonium chloride.

(7) Step 7

This step [(7) in reaction scheme (I)] is the reaction for hydrogenating the compound (IIa) having a protected (for example, acylated) monosaccharide residue and protecting group for hydroxyl group to obtain an esculetin derivative (Ia) having a protected (for example, acylated) monosaccharide residue. This reaction is performed by a reaction with hydrogen gas in the presence of a palladium or platinum catalyst at 4° to 80° C. for 0.5 to 48 hours. The palladium catalyst used is preferably palladium-barium sulfate, palladium-carbon, or the like.

(8) Step 8

This step [(8) in reaction scheme (I)] is the reaction for removing the protecting group from (for example, deacylating) the compound (IIa) having a protected (for example, acylated) monosaccharide residue and protecting group for hydroxyl group [wherein $R^5$ is a protected (for example, acylated) monosaccharide residue] to obtain a compound (IIb) having a monosaccharide residue and protecting group for hydroxyl group (wherein $R^4$ is a monosaccharide residue). This reaction, for example, is performed by dissolving the compound (IIa) in an organic solvent such as methanol and then performing a reaction with alkali metal, such as potassium or sodium, dissolved in alcohol such as methanol while passing a stream of inert gas (for example, nitrogen gas or argon gas). The reaction temperature is generally 4° to 70° C. and the reaction time generally 0.1 to 72 hours.

(9) Step 9

This step [(9) in reaction scheme (I)] is the reaction for hydrogenating the compound (IIb) having the monosaccharide residue and protecting group for hydroxyl group to obtain the esculetin derivative (Ib) having the monosaccharide residue. This reaction is performed with hydrogen gas in the presence of a palladium or platinum catalyst at 4° to 70° C. for 0.1 to 48 hours. The palladium catalyst used is preferably palladium-barium sulfate, palladium-carbon, or the like.

If step 9 is performed after converting the monosaccharide residue of the compound (IIb) to another monosaccharide residue or protecting the hydroxyl group of the monosaccharide residue, it is possible to obtain a compound (Ib) having another monosaccharide residue or protected monosaccharide residue. For example, when the monosaccharide residue has —CH₂OH, it is possible to obtain a compound having a monosaccharide residue containing —COOH by oxidizing this group —CH₂OH to —COOH. For example, it is possible to oxidize the glucose residues and convert to glucuronic acid residues.

As the reactions for protecting a hydroxyl group of a monosaccharide residue, there are acylation and acetalization. Acylation may be performed basically in the same manner as in step 3. An example of acetalization is a reaction of 6-(β-2-acetoamide-2-deoxy-D-glucopyranosyloxy)-7-benzyloxycoumarin (IIb-2) and an aldehyde compound of the formula $$R^{18}CHO$$

wherein $R^{18}$ having the same meaning as above, to obtain a compound having a 6-membered ring formed by the acetalized 4- and 6-hydroxyl groups of the monosaccharide residue. The resulting compound has a structure of the formula

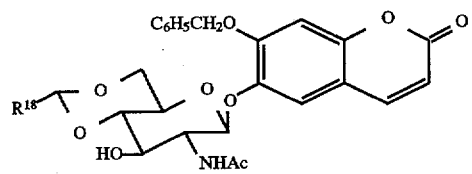

(10) Step 10

This step [(10) in reaction scheme (I)] is the reaction for removing the protecting group from (for example, deacylating) the esculetin derivative (Ia) having a protected (for example, acylated) monosaccharide residue to obtain an esculetin derivative (Ib) having a monosaccharide residue. This reaction can basically be performed in the same manner as step 8.

Examples of the reactions will be shown for step 6, which is an important step for obtaining the novel compounds of the present invention.

REACTION EXAMPLE 1

Preparation of 6-β-2,3,4,6-tetra-O-acetyl-D-galactosyloxy)-7-benzyloxycoumarin [IIa-1] from 7-benzyloxy-6-hydroxycoumarin [III-1] and 2,3,4,6-tetra-O-acetyl-1-bromo-α-D-galactose [IV-1]

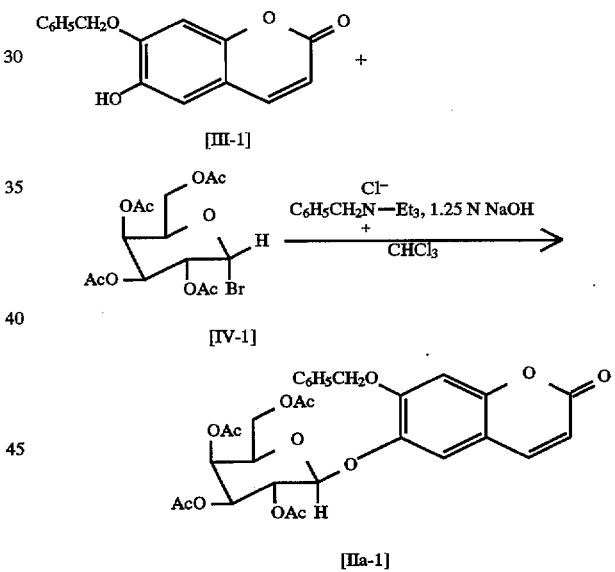

REACTION EXAMPLE 2

Preparation of 6-(β-2-acetoamide-3,4,6-tri-O-acetyl-2-deoxy-D-glucopyranosyloxy)-7-benzyloxycoumarin [IIa-2] from 7-benzyloxy-6-hydroxycoumarin [III-1] and 2-acetoamide-3,4,6-tri-O-acetyl-1-chloro-2-deoxy-α-D-glucopyranose [IV-2]

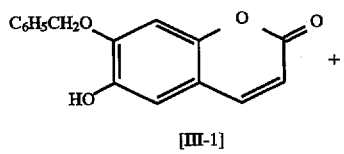

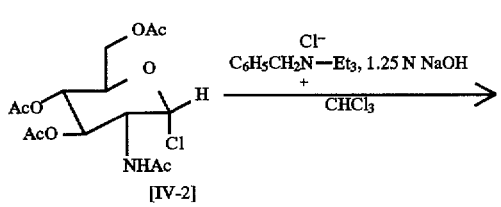

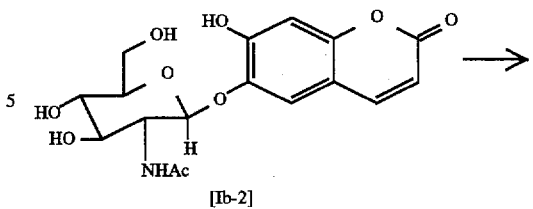

REACTION EXAMPLE 3

Preparation of 6-(β-2-acetoamide-3,4,6-tri-O-acetyl-2-deoxy-D-galactosyloxy)-7-benzyloxycoumarin [IIa-3] from 7-benzyloxy-6-hydroxycoumarin [III-1] and 2-acetoamide-3,4,6-tri-O-acetyl-1-chloro-2-deoxy-α-D-galactose [IV-3]

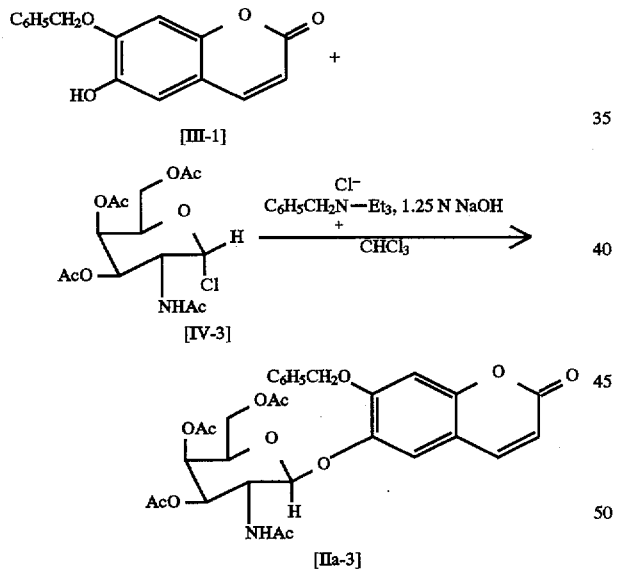

Similarly, it is possible to obtain 6-(β-2-amino-2-deoxy-D-galactosyloxy)-7-hydroxycoumarin [Ib-3'] from 6-(9-2-acetoamide-2-deoxy-D-galactosyloxy)-7-hydroxycoumarin [Ib-3] as follows:

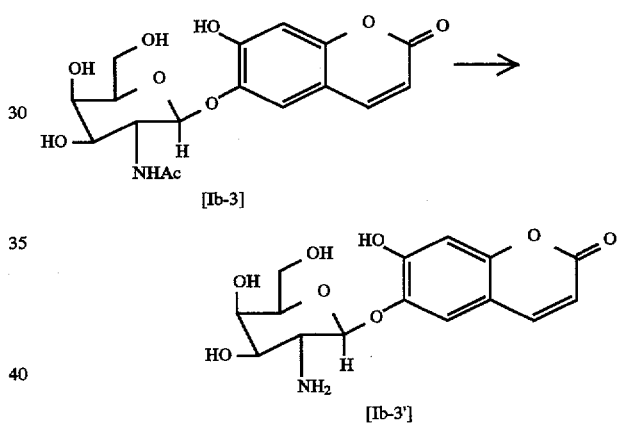

The above deacylation is preferably performed on the compound (IIb) having the protected 7-hydroxyl group. Thereafter, it is possible to perform hydrogenolysis under conditions similar to those of step 9 to obtain an esculetin derivative having an amino sugar residue not including an acyl group. For example, see Examples 19 and 20.

When the monosaccharide residue is an N-acyl amino sugar residue, it is possible to obtain an esculetin derivative having an amino sugar residue not including an acyl group by performing a further deacylation reaction. This reaction is performed between an esculetin derivative having the N-acyl amino sugar residue as a monosaccharide residue and a hydrazine solution, alcoholic potassium or alkaline aqueous solution, preferably 0.1 to 12N NaOH, at 40° to 120° C. for 1 to 48 hours. Therefore, it is possible to obtain 6-(β-2-amino-2-deoxy-D-glucosyloxy)-7-hydroxycoumarin [Ib-2'] from 6-(β-2-acetoamide-2-deoxy-D-glucosyloxy)-7-hydroxycoumarin [Ib-2] by the following reaction:

It is known that the cartilage matrix components are negatively charged. In view of the affinity to the cartilage tissue and accumulating properties, a salt of an inorganic or organic acid with an esculetin derivative having an amino sugar residue not including an acyl group is useful as the compounds having positive charges.

(B) Preparation of diglycoside (B-1) Method from esculetin or 4-substituted esculetin as a starting material The reaction scheme (II) is shown as follows:

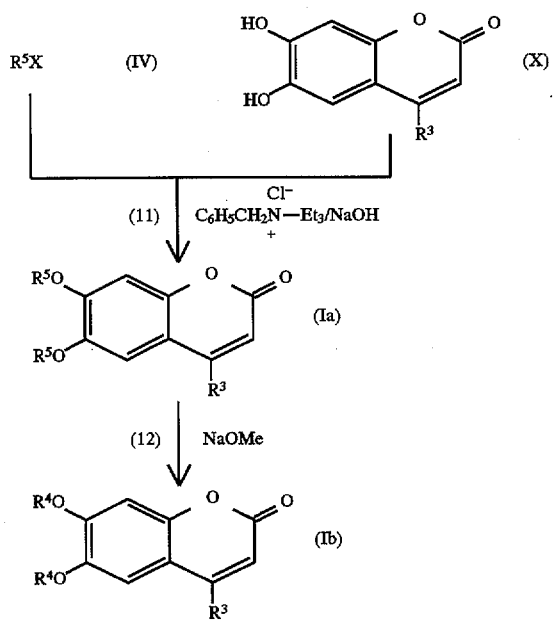

The reaction scheme (III) is as follows:

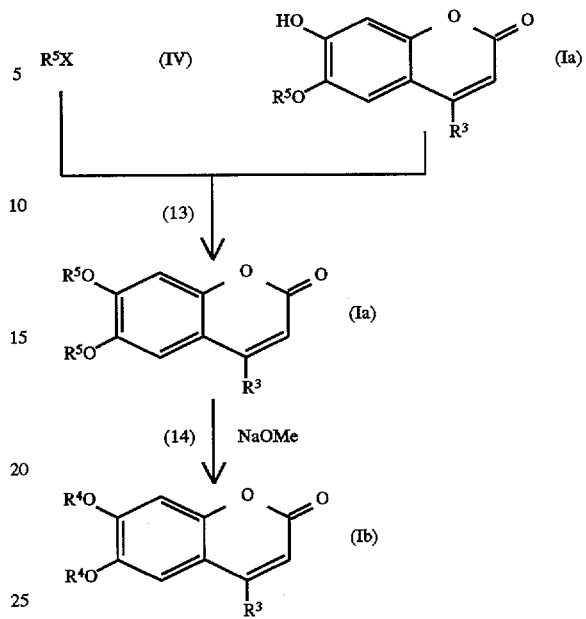

The steps (11) to (12) in the above reaction scheme (II) will be explained hereinafter as steps 11 to 12.

(11) Step 11

This step [(11) in reaction scheme (II)] is a reaction for introducing protected (for example, acylated) monosaccharide residues to the 6- and 7-hydroxyl groups of esculetin or 4-substituted esculetin compound (X) to obtain the esculetin derivative (Ia) of the present invention having two same monosaccharide residues. For example, the compound (X) and the monosaccharide derivative (IV) are dissolved in organic solvent such as chloroform. Then, a halogenated ammonium having an organic group dissolved in a caustic alkali aqueous solution is added dropwise to the solution, and a reaction is performed at 4° to 120° C. for 1 to 72 hours to obtain the compound (Ia). The monosaccharide derivative is used in an amount of at least 2 molars with respect to the amount of the compound (X) used. An example of the caustic alkali aqueous solution is a sodium hydroxide aqueous solution, and an example of the halogenated ammonium having an organic group is benzyltriethylammonium chloride.

(12) Step 12

This step [(12) of the reaction scheme (II)] is a reaction for removing the protecting group from (for example, deacylating) the protected (acylated) esculetin derivative (Ia) of the present invention having two same monosaccharide residues to obtain the esculetin derivative (Ib) of the present invention having two same monosaccharide residues. This reaction is performed with an alkali metal such as a potassium or sodium dissolved in alcohol such as methanol while passing an inert gas, after dissolving the compound (Ia) in organic solvent such as methanol. The reaction temperature is generally 4° to 70° C. and the reaction time is generally 0.1 to 72 hours.

(B-2) Method from monoglycoside derivatives as a starting material

The steps (13) and (14) of the above reaction scheme (III) correspond to the step 13 and step 14 explained hereinafter. The above reaction scheme (III) shows the case of introduction of a protected (for example, acylated) monosaccharide to the 7-hydroxy group in step 13, but a reaction step for replacing the 6- and 7-substituent groups is also a reaction step of the present invention.

(13) Step 13

This step [(13) in reaction scheme (III)] is a reaction for introducing the same or different protected (for example, acylated) monosaccharide residues to the hydroxyl groups of the esculetin derivatives (Ia) of the present invention having one protected (for example, acylated) monosaccharide residue. This process makes it possible to obtain the esculetin derivative (Ia) of the present invention having two same or different protected (for example, acylated) monosaccharide residues. The reaction reagents and the reaction conditions are basically similar to those of step 6. However, it is preferable to use a basic catalyst such as triethylamine instead of a phase transfer catalyst.

(14) Step 14

This step [(14) in reaction scheme (III)] is a reaction for removing the protecting group from (for example, deacylating) the esculetin derivative (Ia) of the present invention having two same or different protected (for example, acylated) monosaccharide residues to obtain the esculetin derivative (Ib) of the present invention having two same or different monosaccharide residues. The reaction reagents and the reaction conditions are basically similar to those of step 12.

Examples of the reactions will be shown for step 11 and step 13, which are important steps for obtaining the novel compounds of the present invention.

REACTION EXAMPLE 4

Preparation of 6,7-bis(β-2,3,4,6-tetra-O-acetyl-D-galactosyloxy)coumarin, [Ia-4] from esculetin [X-1] and 2,3,4,6-tetra-O-acetyl-1-bromo-α-D-galactose [IV-1]

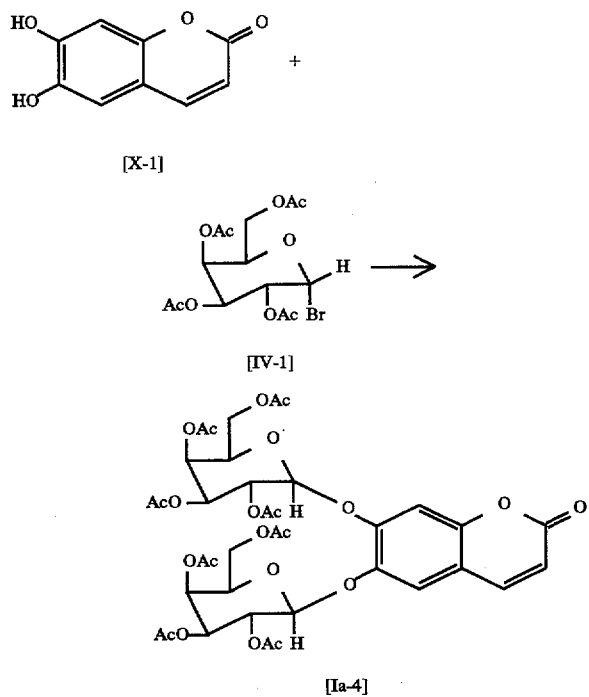

REACTION EXAMPLE 5

Preparation of 7-(β-2,3,4,6-tetra-O-acetyl-D-galactosyloxy)-6-(β-2-acetoamide-3,4,6-tri-O-acetyl-2-deoxy-D-glucopyranosyloxy)coumarin [Ia-5] from 6-(β-2-acetoamide-3,4,6-tri-O-acetyl-2-deoxy-D-glucopyranosyloxy)-7-hydroxycoumarin [Ia-2] and 2,3,4,6-tetra-O-acetyl-1-bromo-α-D-galactose [IV-1]

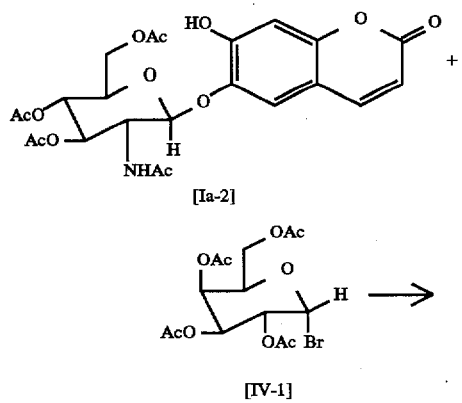

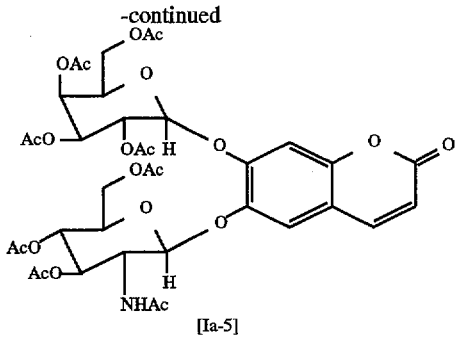

The free esculetin derivative of the present invention may be converted to the corresponding salt, a salt may be converted into other salt, and the salt of the esculetin derivative of the present invention may be converted to free esculetin derivative, by the processes which per se are known. For example, a salt may be formed form the esculetin derivative having 6- or 7-hydroxy group (phenolic hydroxy group) or the esculetin derivative having N-acetyl glucosamine or uronic acid residue containing a free carboxylic acid group. More particularly, a phenolic hydroxy group or a free carboxylic acid group can be converted to an alkaline salt by reacting the above esculetin derivative with equimolar alkali hydroxide, such as sodium or potassium hydroxide. Further, the salt can be converted to a free compound by acidifying the salt solution with hydrochloric or sulfuric acid. The compound having a free amino group may be reacted with equal amount of an organic acid, such as malic, citric or acetic acid to form the corresponding salt. An inorganic acid, such as hydrochloric or sulfuric acid may be used to form hydrochloride or sulfate The inorganic salt can be converted to a free base by treatment with an alkali. The salt is water soluble, whereas the free compound is slightly soluble in water, and thus can be isolated by precipitation.

As the method to purify the reaction product, extraction, chromatography, recrystallization, or reprecipitation may be used. The structure of the purified product may be confirmed by, for example, the infrared absorption spectrum, ultraviolet absorption spectrum, nuclear magnetic resonance absorption spectrum, elemental analysis, or mass spectrum.

The toxicity of the esculetin derivatives of the present invention was examined. Typical examples of the present derivatives were administered orally at a dose of 2000 mg/kg (body weight) to male mice and male rats which were then observed for seven days. No deaths and no remarkable toxicity were observed. The esculetin derivatives of the present invention are extremely safe compounds (see Example 27).

The esculetin derivatives exhibit, as a pharmacological effect, the function to inhibit destruction of cartilage in mouse FHC models (see Example 28).

Accordingly, the esculetin derivatives of the present invention or pharmaceutically acceptable salts thereof are useful as effective ingredients of chondroprotective agents for treating various types of arthropathy accompanying the cartilage destruction of the joints. Examples of such arthropathy include rheumatoid arthritis, osteoarthritis, periarthritis humeroscapularis, shoulder-arm-neck syndrome, lumbago, or the like.

The pharmaceutical composition having as an effective ingredient the esculetin derivative of the present invention or pharmaceutically acceptable salts thereof, particularly the chondroprotective agent, may be in the form of any conventional formulation. The pharmaceutical composition may contain the derivative alone, or a mixture of the derivative with any pharmaceutically acceptable carrier or diluent. The amount of the effective ingredient in the composition is not particularly limited, but may for example be 0.01 to 100% by weight, preferably 0.1 to 70% by weight.

The pharmaceutical composition, in particular the chondroprotective agent, of the present invention may be administered orally or parenterally.

The dose of the pharmaceutical composition, in particular the chondroprotective agent, of the present invention varies with the patient (mammal, particularly humans), age, individual differences, state of illness, and the like. Generally speaking, however, when a human is treated, the dose of oral administration of the esculetin derivative of the present invention is in the range of 0.1 to 500 mg/kg (body weight) per day, preferably 0.5 to 200 mg/kg (body weight), which is usually divided into 1 to 4 dosages in a day, although the dose outside the above range may sometimes be administered.

EXAMPLES

The present invention now will be further illustrated by, but is by no means limited to, the following Examples.

In the following Examples, Ac means acetyl, Me means methyl, Ph means phenyl, Glc means glucosyl, and Ar means aryl.

Example 1

Preparation of 7-benzyloxy-6-hydroxycoumarin [III-1] (Steps 1 and 2)

Esculin [VIII] (1.0 g), benzyl chloride (1.0 g), potassium carbonate (0.7 g), a catalytic amount of 18-crown-6-ether and potassium iodide, and dimethylformamide (40 ml) were added to an eggplant-shaped flask (100 ml). The mixture was stirred at 60° C. for 8 hours to cause a reaction. The reaction mixture was concentrated under reduced pressure and the residue was poured into ice water. The precipitated crystals were filtered out and recrystallized from methanol to obtain 7-benzyloxy-6-D-glucosyloxycoumarin (VII-1) (melting point=184° to 186° C, mass spectrum ($M^+$)=430, yield =86.4%).

The compound [VII-1] (0.6 g) was heated under reflux for one hour in a mixture of methanol (35 ml) and 10% hydrochloric acid (35 ml). The reaction mixture was concentrated under reduced pressure. The crystals were filtered out, and the above-captioned compound [III-1] (yield= 90.3%) was obtained.

Melting point: 193°–195° C.

Mass spectrum ($M^+$): 268

Example 2

Preparation of 2,3,4,6-tetra-O-acetyl-1-bromo-α-D-galactose [IV-1] (Steps 3 and 4 wherein a sugar component is galactose)

The above-captioned compound was prepared from D-galactose [VI-1] in accordance with the method described in Whistler & Wolfrom, Methods in Carbohydrate Chemistry, Vol. I, pp. 224 to 225 (1963).

More particularly, D-galactose [VI-1] (18 g), acetic anhydride (90 ml), and anhydrous pyridine (130 ml) were added to a round-bottom flask (2000 ml), and the reaction was carried out at room temperature for 36 hours. After the reaction was completed, the solvents were completely removed to obtain 1,2,3,4,6-penta-O-acetyl-D-galactose [V-1] as a mixture of α-anomers and β-anomers. A glacial acetic acid solution of hydrogen bromide gas (90 ml, saturated at 0° C.) was bubbled to the mixture, and a reaction was carried out at room temperature for about 3 hours to obtain the above-captioned compound [IV-1] (40 g, yield= 94%) as crystals.

Melting point: 79°–81° C.

Example 3

Preparation of 6-(β-2,3,4,6-tetra-O-acetyl-D-galactosyloxy)-7-benzyloxycoumarin [IIa-1] (Step 6 wherein a sugar component is galactose)

To an eggplant-shaped flask (500 ml), 7-benzyloxy-6-hydroxycoumarin [III-1] (4.83 g) prepared in Example 1, 2,3,4,6-tetra-O-acetyl-1-bromo-α-D-galactose [IV-1] (14.80 g) prepared in Example 2, and chloroform (180 ml) were added, and the mixture was stirred at room temperature. After 10 minutes, triethylbenzylammonium chloride (1.03 g) dissolved in 1.25N NaOH (36 ml) was added dropwise. The reaction mixture was stirred at room temperature for 6 days. Then, distilled water (180 ml) was added, and the reaction mixture was extracted with methylene chloride (200 ml). The reaction mixture was further extracted with methylene chloride (100 ml) twice. The organic layers were washed with distilled water, dried over anhydrous sodium sulfate, and concentrated under reduced pressure. The residue was purified by silica gel column chromatography [Kiesel gel 60=200 g, diameter=5.5 cm, n-hexyl/ethyl acetate (1:1)] to obtain the above-captioned compound (7.46 g, yield=69.2%) as white crystals.

Melting point: 157°–157.5° C.

Mass spectrum (EI): 598, 555, 538, 331, 169

$^1$H-NMR (CDCl$_3$, δ ppm): 1.77(s, 3H, —Ac), 2.00(s 3H, —Ac), 2.02(s, 3H, —Ac), 2.19(s, 3H, —Ac), 3.95(t, 1H, C-5'), 4.13(dd, 1H, C-6'), 4.24(dd, 1H, C-6'), 4.94(d, 1H, C-1'), 5.08(dd, 1H, C-3'), 5.15(s, 2H, —CH$_2$-Phenyl), 5.44 (d, 1H, C-4'), 5.50(dd, 1H, C-2'), 6.28(d, 1H, C-3), 6.90(s, 1H), 7.25(s, 1H), 7.39(m, 5H), 7.57(d, 1H, C-4)

IR spectrum (KBr, cm$^{-1}$): 3510w, 3112w, 1750s, 1620m, 1570m, 1522s

Example 4

Preparation of 6-(β-2,3,4,6-tetra-O-acetyl-D-galactosyloxy)-7-hydroxycoumarin [Ia-1] (Step 7 wherein a sugar component is galactose)

To an eggplant-shaped flask (100 ml), 6-(β-2,3,4,6-tetra-O-acetyl-D-galactosyloxy)-7-benzyloxycoumarin [IIa-1] (300 mg) prepared in Example 3 and dioxane (25 ml) were added, and the mixture was stirred at room temperature. 10% Pd/C (50 mg) was added to the solution on a water bath, and the mixture was stirred for about 7 hours in a hydrogen atmosphere. After the completion of the reaction was confirmed by thin layer chromatography (TLC), the reaction mixture was filtered through celite. The filtrate was concentrated under reduced pressure to obtain a crude product (299.2 mg) as transparent oil. The crude product was purified by silica gel chromatography [Kieselgel 60=15 g, diameter=2.5 cm, n-hexane/ethyl acetate (1:2)] to obtain transparent oil. To the resulting oil, n-hexane was added and the wall of the flask was rubbed to obtain the above-captioned compound (236.0 mg, yield=92.8%) as white crystals.

Melting point: 92° C.

Mass spectrum (EI): 508, 464, 406, 331, 169

Optical rotation (c=1, CH$_3$OH): −13.2°

$^1$H-NMR (CDCl$_3$, δ ppm): 2.02 (s, 3H, —Ac), 2.08 (s, 3H, —Ac), 2.15 (s, 3H, —Ac), 2.21 (s, 3H, —Ac), 4.10 (d, 1H, C-5'), 4.18 (m, 1H, C-6'), 4.27 (m, 1H, C-6'), 4.94 (d, 1H, C-1'), 5.14 (dd, 1H, C-3'), 5.46 (dd, 1H, C-2'), 5.48(d, 1H, C-4'), 6.28 (d, 1H, C-3), 6.58 (s, 1H, —OH), 6.92 (s, 1H), 7.05 (s, 1H), 7.54 (d, 1H, C-4)

IR spectrum (KBr, cm$^{-1}$): 3500w, 1750s, 1620m, 1580m, 1520m, 1380m, 1220s

Example 5

Preparation of 6-β-D-galactosyloxy-7-benzyloxycoumarin [IIb-1] (step 8 wherein a sugar component is galactose)

Metal sodium (60 mg) and absolute methanol (60 ml) were added to an eggplant-shaped flask (100 ml) and the mixture was stirred at room temperature under an argon gas stream. 6-(β-2,3,4,6-tetra-O-acetyl-D-galactosyloxy)-7-benzyloxycoumarin [IIa-1] (1.50 g) prepared in Example 3 and then methanol were added to the solution, and the mixture was stirred at room temperature for about 1.5 hours. After the completion of the reaction was confirmed by TLC, distilled water (50 ml) was added to the reaction solution to cease the reaction. The reaction mixture was extracted with ethyl acetate (200 ml) twice. Further, the reaction mixture was extracted with ethyl acetate (50 ml) four times. The organic layers were washed with saturated saline, dried over anhydrous sodium sulfate, and concentrated under reduced pressure, to obtain the above-captioned crude product (1.24 g) as white crystals.

Example 6

Preparation of 6-β-D-galactosyloxy-7-hydroxycoumarin [Ib-1] (step 9 wherein a sugar component is galactose)

The crude 6-β-D-galactosyloxy-7-benzyloxycoumarin [IIb-1] (1.24 g) prepared in Example 5 and 10% Pd/C (124 mg) were added to an eggplant-shaped flask (300 ml). Then, methanol (124 ml) and distilled water (13 ml) were gently poured. The mixture was stirred in a hydrogen atmosphere at room temperature overnight. After the completion of the reaction was confirmed by TLC, the reaction mixture was filtered through celite and the filtrate concentrated under reduced pressure to obtain a yellow crude crystal (890 mg). The crude crystal was recrystallized from distilled water to obtain the above-captioned compound (545.8 mg, yield=55.7%) as white crystals.

Melting point: 144°–147° C.

Mass spectrum (FAB, M+1): 341

Optical rotation (c=1, CH$_3$OH): −71.5°

$^1$H-NMR (CDCl$_3$, δ ppm): 3.60 (dd, 1H, C-3'), 3.70 (m, 1H, C-5'), 3.75 (d, 1H, C-6'), 3.78 (d, 1H, C-6'), 3.85 (dd, 1H, C-2'), 3.90 (d, 1H, C-4'), 4.79 (d, 1H, C-1'), 6.22 (d, 1H, C-3), 6.81 (s, 1H), 7.45 (s, 1H), 7.83 (d, 1H, C-4)

IR spectrum (KBr, cm$^{-1}$): 3350s, 1700s, 1560m, 1300m, 1080s

Example 7

Preparation of 2-acetoamide-1,3,4,6-tetra-O-acetyl-2-deoxy-α-D-glucopyranose [V-2] (step 3 wherein a sugar component is glucosamine)

A solution of a mixture of acetic anhydride (12.25 g) and dry pyridine (18.98 g) was added to an eggplant-shaped flask (500 ml), and then N-acetyl-D-glucosamine [VI-2] (4.43 g) was added at room temperature portionwise. The resulting solution was stirred at room temperature overnight. The reaction solution was poured onto ice water (150 ml), and then, extracted with ether (100 ml) twice. The aqueous layer was concentrated under reduced pressure at 65° C. to obtain the crude product (9.407 g). The crude product was dissolved in ethyl acetate (150 ml). The resulting solution was washed with water (5 ml), dried over sodium sulfate, and further dried under reduced pressure by a rotary evaporator to obtain oil. Ether was added to the oil and the substance was triturated to obtain the above-captioned compound (6.47 g, yield=83.1%) as white crystals.

Rf: 0.39 (ethyl acetate)

Melting point: 185°–187° C.

$^1$H-NMR (CDCl$_3$, δ ppm): 1.94 (s, 3H), 2.04 (s, 3H), 2.06 (s, 3H), 2.09 (s, 3H), 2.20 (s, 3H), 4.00 (m, 1H, C5-H), 4.07 (d, 1H, C6-H), 4.25 (dd, 1H, C6-H), 4.48 (dt, 1H, C2-H), 5.23 (m, 2H, C3, 4-H), 5.72 (d, 1H, NH), 6.17 (d, 1H, C1-H)

IR spectrum (KBr, cm$^{-1}$): 3360s, 3025m, 2980m, 1740s, 1675s, 1520s, 1425s, 1380s, 1230s, 1130s, 1025s, 940s, 890m, 840m

Example 8

Preparation of 2-acetoamide-3,4,6-tri-O-acetyl-1-chloro-2-deoxy-α-D-glucopyranose [IV-2] (step 4 wherein a sugar component is glucosamine)

Acetic anhydride (6 ml) was added to an eggplant-shaped flask (50 ml). Dry hydrogen chloride gas was blown into the acetic anhydride to saturate it. There was an approximately 1.5 g increase in weight, To the solution, 2-acetoamide-1,3,4,6-tetra-O-acetyl-2-deoxy-α-D-glucopyranose [V-2] prepared in Example 7 (2.0 g) was added and the mixture was stirred at room temperature for 6 days. Methylene chloride (25 ml) was added to the reaction mixture and the reaction mixture was washed with a saturated sodium hydrogencarbonate aqueous solution (20 ml) twice. The collected organic layers were dried over anhydrous sodium sulfate, and concentrated to obtain a crude product (1.32 g). The crude product was purified by silica gel chromatography [diameter=2.5 cm, length=10.5 cm, silica gel=15 g, n-hexane/ethyl acetate (1:4)] to obtain the above-captioned compound (871.7 mg, yield=46.4%) as white crystals.

Rf: 0.67 (ethyl acetate)

Melting point: 125°–126° C.

Mass spectrum (m/e): 731 (2M+1), 356 (100), 324, 306, 228, 168, 150

$^1$H-NMR (CDCl$_3$, δ ppm): 1.99 (s, 3H), 2.06 (s, 6H), 2.11 (s, 3H), 4.14 (d, 1H, C5-H), 4.28 (m, 2H, C6-H), 4.54 (dt, 1H, C2), 5.22 (t, 1H, C4-H), 5.33 (t, 1H, C3-H), 5.98 (d, 1H), 6.19 (d, 1H, C1-H)

IR spectrum (KBr, cm$^{-1}$): 3300w, 1750s, 1650m, 1550m, 1440m, 1380m, 1295m, 1235s, 1215s, 1120m, 1035m, 980w, 918w, 895w

Example 9

Preparation of 2-acetoamide-3,4,6-tri-O-acetyl-1-chloro-2-deoxy-α-D-glucopyranose [IV-2] (step 5 wherein a sugar component is glucosamine)

Acetyl chloride (25 ml) was poured in an eggplant-shaped flask (200 ml) and then N-acetyl-D-glucosamine (VI-2) (12.5 g) was added portionwise under stirring. After 4 hours, the reaction solution generated heat and a gentle reflux occurred. The reaction solution was stirred overnight, whereupon a light red viscous solid was obtained. Methylene chloride (100 ml) was added to the solid to dissolve it. The solution was neutralized with a cold saturated sodium hydrogencarbonate aqueous solution. The collected organic layers were washed with distilled water, dried over anhydrous sodium sulfate, and then concentrated to obtain a crude product (23.8 g). The crude product was crystallized from ether to obtain the above-captioned compound (16.0 g, yield=77%) as white crystals.

Example 10

Preparation of 6-(β-2-acetoamide-3,4,6-tri-O-acetyl-2-deoxy-D-glucomyranosyloxy)-7-benzyloxycoumarin [IIa-2] (step 6 wherein a sugar component is glucosamine)

To an eggplant-shaped flask (25 ml), 2-acetoamide-3,4,6-tri-O-acetyl-1-chloro-2-deoxy-α-D-glucopyranose [IV-2] (914.5 mg) prepared in Example 8 or 9, 7-benzyloxy-6-hydroxycoumarin [III-1] (335.5 mg), and chloroform (10 ml) were added to produce a suspension. Benzyltriethylammonium (113.9 mg) dissolved in 1.25N NaOH (12.5 ml) was added to the suspension. The suspension was refluxed in an argon atmosphere for 3 hours, and then allowed to cool to room temperature. The reaction mixture was diluted with methylene chloride (40 ml), and the organic layer was separated. The aqueous layer was extracted with methylene chloride (20 ml). The collected organic layers were washed with saturated saline (10 ml), dried over anhydrous sodium sulfate, and concentrated to obtain a crude product (1.16 g). The crude product was treated with methanol/methylene chloride to obtain the above-captioned compound (150.4 mg, yield=21.1%) as white needle crystals.

Rf: 0.56 (ethyl acetate)

Melting point: 224°–227° C.

Mass spectrum (m/e): 597, 537, 523, 419, 329, 268, 209, 167, 125 (100) $^1$H-NMR (CDCl$_3$, δ ppm): 1.54 (s, 3H), 2.02 (s, 3H), 2.03 (s, 3H), 2.04 (s, 3H), 3.07 (m, 1H, C5-H), 4.14 (m, 2H, C-6, C2-H), 4.26 (dd, 1H, C6-H), 5.04 (d, 1H, C1-H), 5.13 (s, 2H, benzyl), 5.11 (q, 1H, C4-H), 5.23 (t, 1H, C3-H), 6.29 (d, C3), 6.92 (s, 1H), 7.26 (s, 1H), 7.46 (m, 5H), 7.59 (d, C4)

IR spectrum (KBr, cm$^{-1}$): 3300m, 2975w, 2900w, 1740s, 1660s, 1620s, 1555m, 1520m, 1440m, 1380s, 1230s, 1180m, 1140m, 1120m, 1060s, 1040s, 930m, 900m, 870m, 810s, 730m Example 11

Preparation of 6-(β-2-acetoamide-3,4,6-tri-O-acetyl-2-deoxy-D-glucopyranosyloxy)-7-hydroxycoumarin [Ia-2] (step 7 wherein a sugar component is glucosamine)

To an eggplant-shaped flask (100 ml), 6-(β-2-acetoamide-3,4,6-tri-O-acetyl-2-deoxy-D-glucopyranosyloxy)-7-benzyloxycoumarin [IIa-2] prepared in Example 10 (871 mg), 10% Pd/C (30 mg), and methyl alcohol (80 ml) were added. The mixture was stirred in a hydrogen atmosphere at room temperature for 4 hours, whereupon the starting material disappeared. The reaction solution was filtered to remove the Pd/C and the filtrate was concentrated under reduced pressure to obtain a crude product (749 mg). The crude product was separated by silica gel chromatography (diameter=3.0 cm, length=10 cm, silica gel=10 g, methylene chloride/methanol=95:5) and was recrystallized from ethanol/methanol to obtain the above-captioned compound (503.4 mg, yield=70.0%) as light yellow needle crystals.

Melting point: 225°–227° C.

Rf: 0.36 (methylene chloride/methanol (95:5))

Mass spectrum (m/e, FAB): 508 (M+1), 460, 330, 289, 273, 242, 210, 154 (100)

Elemental analysis for $C_{23}H_{25}O_{12}N$ Found: C 53.89, H 4.89, N 2.61 Calculated: C 54.44, H 4.97, N 2.76

$^1$H-NMR (CDCl$_3$, δ ppm): 1.95 (s, 3H), 2.02 (s, H), 2.03 (s, 3H), 3.97 (m, 1H, C2-H), 4.14 (m+t, 2H, C5-H, C6-H), 4.32 (dd, 1H, C6-H), 5.08 (t, 1H, C4-H), 5.27 (d, 1H, C1-H), 5.36 (t, 1H, C3-H), 6.21 (d, 1H, coumarin), 6.79 (s, 1H, coumarin), 7.30 (s, 1H, coumarin), 7.81 (d, 1H, coumarin)

IR spectrum (KBr, cm$^{-1}$): 3320s, 3090w, 2950w, 2900w, 1750s, 1705s, 1665s, 1625m, 1610m, 1560s, 1515s, 1440s, 1410m, 1370s, 1295s, 1220s, 1140m, 1090s, 1050s, 980w Example 12

Preparation of 6-(β-2-acetoamide-2-deoxy-D-glucopyranosyloxy)-7-benzyloxycoumarin [IIb-2] (step 8 wherein a sugar component is glucosamine)

To an eggplant-shaped flask (100 ml), 6-(β-2-acetoamide-3,4,6-tri-O-acetyl-2-deoxy-D-glucopyranosyloxy)-7-benzyloxycoumarin [IIa-2] (351 mg) prepared in Example 10 and methanol (90 ml) were added to produce a suspension. Five drops of a methanol solution of sodium methoxide (28%) were added to the suspension. The suspension was heated to 40° C. and stirred. The reaction solution became transparent after 10 minutes and a white precipitate was formed after 20 minutes. The reaction solution was stirred at room temperature for 1.5 hours, and then neutralized with 0.1N HCl. The precipitate was collected by filtration through a glass filter, washed with methanol, and dried under reduced pressure to obtain the above-captioned compound (262.6 mg, yield=95.1%) as white needle crystals.

Melting point: 244°–246° C.

Rf: 0.73 (chloroform/methanol/water (7:3:0.5))

Mass spectrum (m/e): 472 (M+1), 382, 269, 253, 204, 185, 168, 138, 91

$^1$H-NMR (d6-DMSO, δ ppm): 1.73 (s, 3H, N—Ac), 3.23 (q, 1H), 3.43 (t, 1H), 3.51 (m, 1H), 3.73 (q, 2H), 5.02 (d, 1H), 5.25 (s, 2H, benzyl), 6.30 (d, 1H, coumarin), 7.12 (s, 1H, coumarin), 7.31 (t, 1H, para-benzyl), 7.39 (t, 2H, metabenzyl), 7.43 (s, 1H, coumarin), 7.48 (d, 2H), 7.79 (d, 1H, AcNH), 7.89 (d, 1H, coumarin)

IR spectrum (KBr, cm$^{-1}$): 3405s, 3275m, 2900w, 1750s, 1665s, 1615m, 1540m, 1430m, 1390m, 1380m, 1310s, 1270s, 1240w, 1175m, 1110m, 1090s Example 13

Preparation of 6-(β-2-acetoamide-2-deoxy-D-glucopyranosyloxy)-7-hydroxycoumarin [Ib-2] (step 9 wherein a sugar component is glucosamine)

To an eggplant-shaped flask (100 ml), 6-(β-2-acetoamide-2-deoxy-D-glucopyranosyloxy)-7-benzyloxycoumarin [IIb-2] (315.5 mg) prepared in Example 12 and 15% water-containing dimethoxyethane (60 ml) were added to produce a solution. 10% Pd/C (24 mg) was added to the solution and the mixture was stirred in a hydrogen atmosphere at room temperature for 1 hour. The solvent was removed from the reaction mixture under reduced pressure to obtain gray powder. To the resulting powder, a mixture (435 ml) of water/tetrahydrofuran/methanol (5:1:0.2) was added. The powder was dissolved by heating to 75° C. The catalyst was filtered out. The filtrate was concentrated to 50 ml and allowed to stand overnight in a refrigerator to obtain the above-captioned compound (228.0 mg, yield=89.3%) as white needle crystals.

Rf: 0.56 (chloroform/methanol/water (7:3:0.5))

Melting point: 265°–266° C.

Elemental analysis for $C_{17}H_{19}O_9N$ Found: C 53.25, H 4.91, N 3.55 Calculated: C 53.55, H 5.02, N 3.67

$^1$H-NMR (CDCl$_3$, δ ppm): 1.83 (s, 3H), 3.23 (t, 1H, C3-H), 3.35 (m, 1H), 3.48 (t, 1H), 3.52 (m, 1H), 5.00 (d, 1H, C1-H), 6.24 (d, 1H, coumarin), 6.83 (s, 1H, coumarin), 7.36 (s, 1H, coumarin), 7.88 (d, 1H)

IR spectrum (KBr, cm$^{-1}$): 3375s, 3240w, 2930w, 1640s, 1665s, 1600s, 1550m, 1405m, 1275m, 1255m, 1225w, 1172w, 1140w, 1120m, 1085m, 1042m, 1025w, 995m, 930m, 890m, 861m, 820m

Example 14

Preparation of 6,7-bis(β-2-acetoamido-3,4,6-tri-O-acetyl-2-deoxy-α-D-glucopyranossyloxy)coumarin [Ia-6] (step 13 wherein both sugar components are glucosamine)

Acetonitrile (100 ml) was added to 6-(β-2-acetoamide-3,4,6-tri-O-acetyl-2-deoxy-D-glucopyranosyloxy)-7-hydroxycoumarin [Ia-2] (2.15 g) prepared in Example 11 and 2-acetoamide-3,4,6-tri-O-acetyl-1-chloro-2-deoxy-α-D-glucopyranose [IV-2] (2.33 g) prepared in Example 9, and the mixture was stirred under an argon gas stream at room temperature. After 10 minutes, triethylamine (4.29 g) was added dropwise. The mixture was stirred overnight. After the completion of the reaction was confirmed by TLC, ion-exchange resin (CG-50; 5 g) was added to cease the reaction. The ion-exchange resin was removed by G4 glass filter. Then, the filtrate was concentrated under reduced pressure to obtain crude oil (5.09 g). The crude oil was treated by silica gel chromatography (Kieselgel 60=100 g, diameter=6.5 cm, ethyl acetate 100%). The solution was concentrated under reduced pressure, and then, methanol was added to obtain the above-captioned compound (2.30 g, yield=53.5%) as white crystals.

Melting point: 242°–243° C.

Rf: 0.37 (ethyl acetate, 100%)

Mass spectrum (m/e, FAB): 837 (M+1), 330

$^1$H-NMR (DMSO-d6, δ ppm): 1.82 (s, 3H, NHAc), 1.84 (s, 3H, NHAc), 1.96 (s, 3H, Ac), 1.97 (s, 3H, Ac), 1.99 (s, 3H, Ac), 2.00 (s, 3H, Ac), 3.85 (dd, 1H, C2'), 4.01 (m, 4H, C2, C5', C6, C6'), 4.21 (m, 3H, C5, C6, C6'), 4.93 (t, 1H, C4'), 4.98 (t, 1H, C4), 5.31 (m, 2H, C3, C3'), 5.45 (d, 1H, C1'), 5.55 (d, 1H, C1), 6.39 (d, 1H, coumarin), 7.29 (s, 1H, coumarin), 7.48 (s, 1H, coumarin), 7.94 (d, 2H, coumarin, NH), 8.08 (d, 1H, NH)

IR spectrum (KBr, cm$^{-1}$): 3320m, 1750s, 1670m, 1555m, 1435w, 1380m, 1285m, 1240s, 1040s

Example 15

Preparation of 7-benzyloxy-6-hydroxy-4-methylcoumarin [III-2] (introduction of protecting group in 7-hydroxyl group)

4-methylesculetin [X-2] (5.0 g) was dissolved in dimethylformamide 52 ml). To the solution sodium carbonate (1.80 g) was added at room temperature. Benzyl chloride (4.94 g) was added dropwise at 10° C. under stirring, and the mixture was stirred overnight. After the reaction product was confirmed by TLC, the reaction solution was poured into ice water, and extracted with chloroform. The organic layer was washed with saturated saline, dried over anhydrous sodium sulfate, and concentrated under reduced pressure. Chloroform was added to the residue, and the insolubles were separated by filtration. The insolubles were recrystallized from ethanol to obtain the above-captioned compound (0.85 g, yield=11.6%). The mother solution was purified by column chromatography [Kiesel gel, Merck Co., chloroform/ethyl acetate (24:1)] to isolate the reaction products at 6-position and 6,7-position.

(1) Above-captioned compound [III-2] (reaction product at 7-position)

Rf: 0.46 (chloroform/ethyl acetate (12:1))

$^1$H-NMR (DMSO-d6, δ ppm): 2.33 (s, 3H, C4-Me), 5.24 (s, 2H, C7-CH$_2$), 6.17 (s, 1H, C3-H), 7.05 (s, 1H, C8-H, C5-H), 7.34 (m, 1H, Aromatic), 7.41 (m, 2H, Aromatic), 7.51 (m, 2H, Aromatic), 9.42 (s, 1H, C6-OH)

$^{13}$C-NMR (DMSO-d6, δ ppm): 18.14 (C4-Me), 70.02 (C7-CH$_2$), 101.40 (C8), 109.41 (C5), 111.32 (C10), 112.52 (C3), 127–128 (Aromatic), 136.36 (Aromatic), 143.71 (C7), 147.37 (C4), 150.37 (C6), 152.98 (C9), 160.42 (C2)

(2) reaction product at 6-position

Rf: 0.37 (chloroform/ethyl acetate (12:1))

$^1$H-NMR (DMSO-d6, δ ppm): 2.35 (s, 3H, C4-Me), 5.19 (s, 2H, C6-CH$_2$), 6.13 (s, 1H, C3-H), 6.81 (s, 1H, C8-H), 7.25 (s, 1H, C5-H), 7.34 (m, 1H, Aromatic), 7.41 (m, 2H, Aromatic), 7.51 (m, 2H, Aromatic), 10.34 (s, 1H, C7-OH)

$^{13}$C-NMR (DMSO-d6, D ppm): 18.26 (C4-Me), 70.57 (C6-CH$_2$), 103.01 (C8), 109.14 (C5), 110.50 (C10), 111.21 (C3), 127.87 (Aromatic), 128.35 (Aromatic), 136.87 (Aromatic), 143.97 (C7), 148.92 (C4), 150.37 (C6), 153.38 (C9), 160.39 (C2)

(3) reaction product at 6,7-position

Rf: 0.70 (chloroform/ethyl acetate (12:1))

$^1$H-NMR (DMSO-d6, δ ppm): 2.37 (s, 3H, C4-Me), 5.20 (s, 2H, C6-CH$_2$), 5.26 (s, 2H, C7-CH$_2$), 6.19 (s, 1H, C3-H), 7.15 (s, 1H, C8-H), 7.30 (s, 1H, C5-H), 7.34 (m, 1H, Aromatic), 7.39 (m, 2H, Aromatic), 7.48 (m, 2H, Aromatic)

$^{13}$C-NMR (DMSO-d6, δ ppm): 18.23 (C4-Me), 70.14 (C6-CH$_2$), 70.79 (C7-CH$_2$), 101.75 (C8), 109.32 (C5), 111.43 (C10), 112.22 (C3), 127–131 (Aromatic), 136.32 (Aromatic), 136.84 (Aromatic), 144.89 (C7), 148.75 (C4), 151.88 (C6), 153.18 (C9), 160.20 (C2)

Example 16

Preparation of 7-benzoyloxy-6-(β-2-acetoamide-3,4,6-tri-O-acetyl-2-deoxy-D-glucopyranosyloxy)-4-methylcoumarin [IIa-12] (step 13 wherein a sugar component is glucosamine)

To an eggplant-shaped flask (300 ml), 2-acetoamide-3,4,6-tri-O-acetyl-1-chloro-2-deoxy-α-D-glucopyranose [IV-2] (6.41 g) prepared in Example 8, 7-benzyloxy-6-hydroxy-4-methylcoumarin [III-2] (3.30 g) prepared in Example 15, and dichloromethane (120 ml) were added to produce a suspension. To the suspension, benzyltriethylammonium chloride (1.07 g) dissolved in 1.25N NaOH (38 ml) was added at room temperature under stirring. The mixture was stirred overnight at room temperature and the precipitated crystal was removed by filtration. The mother liquor was decanted and the organic layer was concentrated. The residue and the crystals filtered out were combined and washed with methanol to obtain the above-captioned compound (5.76 g, yield=80.7%) as white crystals.

Melting point: 253°–254° C.

Rf: 0.69 (methanol/ethyl acetate (5:95))

Mass spectrum (m/e, EI): 612 (M$^+$), 330 (Ac-Glc)

$^1$H-NMR (DMSO-d6, δ ppm): 1.70 (s, 1H, N—Ac), 1.95 (s, 3H, C6-Ac), 1.97 (s, 3H, Ac), 2.00 (s, 3H, Ac), 2.41 (d, 3H, C4'-Me), 4.06 (m, 1H, C2-H), 4.09 (d, 1H, C6-H), 4.14 (m, 1H, C5-H), 4.17 (d, 1H, C6-H), 4.96 (t, 1H, C4-H), 5.23 (t, 1H, C3-H), 5.26 (s, 2H, C7'-CH$_2$), 5.38 (d, 1H, C1-H), 6.24 (d, 1H, C'3-H), 7.15 (s, 1H, C8'-H), 7.32 (t, 1H, Aromatic), 7.38 (t, 2H, Aromatic), 7.40 (s, 1H, C5'-H), 7.47 (d, 2H, Aromatic), 8.04 (d, 1H, Ac—NH)

IR spectrum (KBr disk, ν cm$^{-1}$): 3525m, 2940w, 2880w, 1745s, 1658s, 1618s, 1562m, 1538m

Example 17

Preparation of 7-benzyloxy-6-(β-2-acetoamide-2-deoxy-D-glucopyranosyloxy)-4-methylcoumarin [IIb-12] (step 8 wherein a sugar component is glucosamine)

7-Benzyloxy-6-(β-2-acetoamide-3,4,6-tri-O-acetyl-2-deoxy-D-glucopyranosyloxy)-4-methylcoumarin [IIa-12] (0.5 g) prepared in Example 16 was suspended in methanol (40 ml). To the suspension, two drops of a methanol solution of sodium methoxide (28%) were added at room temperature with a Pasteur pipette. After the completion of the reaction was confirmed by TLC, the solution was neutralized with 1N HCl. The precipitated crystals were filtered to obtain the above-captioned compound (0.36 g, yield=92.3%) as white crystals.

Melting point: 263°–264° C.

Rf: 0.66 (chloroform/methanol/water (7:3:1))

Mass spectrum (m/e, FAB): 485 (M+1), 283 (Bn-EST)

$^1$H-NMR (DMSO-d6, δ ppm): 1.73 (s, 1H, N—Ac), 2.37 (d, 3H, C4'-Me), 3.17 (m, 1H, C4-H), 3.36 (m, 1H, C5-H), 3.45 (m, 2H, C3-H, C6-H), 3.77 (m, 2H, C6-H, C2-H), 4.75 (t, 1H, C6-OH), 5.00 (d, 1H, C1-H), 5.07 (d, 1H, C3-OH), 5.14 (d, 1H, C4-OH), 5.24 (s, 2H, C7'-CH$_2$), 6.21 (d, 1H, C'3-H), 7.12 (s, 1H, C8'-H), 7.32 (t, 1H, Aromatic), 7.39 (t, 2H, Aromatic), 7.47 (d, 2H, Aromatic), 7.49 (s, 1H, C5'-H), 7.79 (d, 1H, Ac—NH)

IR spectrum (KBr disk, ν cm$^{-1}$): 3400s, 3290s, 3150m, 2860w, 1730s, 1716s, 1659s, 1618s, 1560s, 1520m

Example 18

Preparation of 7-hydroxyl-6-(β-2-acetoamide-2-deoxy-D-glucopyranosyloxy)-4-methylcoumarin [Ib-12] (step 9 wherein a sugar component is glucosamine)

7-Benzyloxy-6-(β-2-acetoamide-2-deoxy-D-glucopyranosyloxy)-4-methylcoumarin [IIb-12] (0.35 g) prepared in Example 17 was suspended in a 15% water-containing dimethoxyethane (40 ml). To the suspension, 10% Pd/C (10.5 mg) was added. The suspension was stirred under a hydrogen gas atmosphere for 2 hours. After the completion of the reaction was confirmed by TLC, the suspension was dried by an evaporator under reduced pressure to obtain the residue. The residue was dissolved in dioxane/water (1:1) (200 ml) and filtered through celite to remove the catalyst. The filtrate was concentrated under reduced pressure. The resulting crystal was washed with methanol to obtain the above-captioned compound (0.27 g, yield=96.4%) as light gray crystals.

Melting point: 263° C. (decomposition)

Rf: 0.50 (chloroform/methanol/water (7:3:1))

Mass spectrum (m/e, FAB): 396 (M+1)

$^1$H-NMR (DMSO-d6, δ ppm): 1.83 (s, 1H, N—Ac), 2.35 (d, 3H, C4'-Me), 3.16 (m, 1H, C4-H), 3.32 (m, 1H, C5-H), 3.48 (m, 2H, C3-H, C6-H), 3.64 (q, 1H, C2-H), 3.76 (m, 1H, C6-H), 4.70 (m, 1H, C6-OH), 4.96 (d, 1H, C1-H), 5.08 (d, 1H, C3-OH), 5.13 (d, 1H, C4-OH), 6.14 (d, 1H, C'3-H), 6.80 (1H, C8'-H), 7.40 (s, 1H, C5'-H), 7.91 (d, 1H, Ac—NH), 9.74 (s, 1H, C7'-OH)

IR spectrum (KBr disk, ν cm$^{-1}$): 3425s, 3398s, 3275s, 3152s, 3090s, 2950s, 1688s, 1662s, 1660s, 1580s, 1558ss 1522m

Example 19

Preparation of 6-(β-2-amino-2-deoxy-D-glucopyranosyloxy)-7-benzyloxycoumarin hydrochloride [IIb-2'] (deacylation of 2-acetoamide group wherein a sugar component is glucosamine)

To an eggplant-shaped flask (25 ml), 6-(β-2-acetoamide-2-deoxy-D-glucopyranosyloxy)-7-benzyloxycoumarin [IIb-2] (471.5 mg) prepared in Example 12 and ethanol (3 ml) were added to produce a suspension. To the suspension, a newly prepared ethanol solution of 3.02N KOH (6.62 ml) was slowly added dropwise to obtain a yellow solution. The solution was refluxed under an argon atmosphere at 120° C. for 6.5 hours. After the disappearance of the starting material was confirmed, the solution was allowed to cool and the solvent was concentrated under reduced pressure. Distilled water (1 ml) was added to the residue at 0° C., and then concentrated hydrochloric acid (3 ml) was carefully added at 0° C. to adjust a pH to 1. Colorless precipitates (KCl) were formed. The mixture was concentrated by a rotary evaporator under reduced pressure. Then, benzene was further added and the mixture was concentrated again. After thoroughly dried, the solid was extracted with ethanol (20 ml×2). Insolubles (KCl, 1.185 g) were removed through 3G3 glass filter. The filtrate was concentrated to obtain a light brown solid (1.969 g). Ether was added to the resulting solid and the solid was triturated to give powder. The resulting powder was filtered, washed with methylene chloride, and then dried to obtain the above-captioned compound (413 mg, yield=88.6%) as white needle crystals.

Melting point: 170°–172° C. (decomposition)

Rf: 0.58 (chloroform/methanol/water (7:3:0.5))

Mass spectrum (m/e, FAB): 430 (M+1)

$^1$H-NMR (DMSO-d6, δ ppm): 3.06 (dd, 1H, C-2') 3.33 (m, 1H), 3.38 (m, 1H), 3.56 (m, 1H), 5.27 (d, 1H, C-1', β), 5.33 (s, 1H, benzyl CH$_2$), 6.33 (d, 1H, C-3), 7.11 (s, 1H), 7.36 (m, 1H), 7.41 (m, 2H), 7.52 (m, 2H), 7.53 (s, 1H), 7.93 (d, C-4)

IR spectrum (KBr, ν cm$^{-1}$): 3375s, 2910m, 1700s, 1608s, 1550m, 1510s, 1430m, 1390m, 1375m, 1275s, 1235m, 1142m, 1062s, 930w, 820w

Example 20

Preparation of 6-(β-2-amino-2-deoxy-D-glucopyranosyloxy)-7-hydroxycoumarin hydrochloride [Ib-2'] (step 9 wherein a sugar component is glucosamine)

To an eggplant-shaped flask (25 ml), 6-(β-2-amino-2-deoxy-D-glucopyranosyloxy)-7-benzyloxycoumarin hydrochloride [IIb-2'] (359.7 mg) prepared in Example 19 and methanol (10 ml) were added to produce a solution. To the resulting solution, 10% Pd/C (18.6 mg) was added. The mixture was slowly stirred under a hydrogen atmosphere for 2 hours. After the disappearance of the starting material was confirmed, activated carbon (10% w/w) was added. The catalyst was removed through a fluted filter paper. The filtrate was concentrated under reduced pressure to obtain a solid (271.3 mg). The resulting solid was recrystallized from methanol/ether to obtain the above-captioned compound (189.1 mg, yield=65.4%) as light yellow-white powdery crystals.

Melting point: 198°–200° C. (decomposition)

Rf: 0.16 (chloroform/methanol/water (7:3:0.5))

Mass spectrum (m/e, FAB): 340 (M+1)

$^1$H-NMR (DMSO-d6, δ ppm): 3.22 (dd, 1H, C-2'), 3.30 (m, 1H, C-6'), 3.47 (m, 1H, C-4'), 3.65 (m, 1H, C-3'), 3.75 (m, 1H, C-5'), 3.90 (d, 1H), 5.18 (d, 1H, C-1), 6.23 (d, 1H, C-3), 6.84 (s, 1H), 7.46 (s, 1H), 7.84 (d, 1H, C-4)

IR spectrum (KSr, ν cm$^{-1}$): 3320s, 2925s, 1690s, 1627s, 1615s, 1590s, 1565s, 1510s, 1445s, 1415m, 1395m, 1375m, 1300s, 1260s, 1220m, 1180m, 1145s, 1100s, 1070s, 1025s, 970m, 938m, 903m, 880m, 840w, 820w, 762w

Example 21

Preparation of 6-D-(β-glucopyranosideuronate)-7-benzyloxycoumarin [IIb-7] (oxidation of compound with glucose as sugar component to produce a compound with glucuronic acid as sugar component)

The starting material for the present Example, 6-β-D-glucosyloxy-7-benzyloxycoumarin (VII-1), was produced as in Example 1 by reacting esculetin [VIII] and benzyl chloride.

Distilled water/dioxane (1:1) (20 ml) was added to platinum oxide (1.0 g). A medium pressure catalytic reduction apparatus was used for reduction at 1.5 atmospheres for about 3 hours to prepare platinum black.

Distilled water/dioxane (1:1) (100 ml) was added to 6-β-D-glucosyloxy-7-benzyloxycoumarin [VII-1] (1.019 g) and sodium hydrogencarbonate (0.199 g), and the mixture stirred. To the mixture, the above-mentioned platinum black was added. The mixture was placed in an oil bath at 80° C., and oxygen was vigorously blown into the mixture. The oil bath was removed and the mixture was cooled. After ion exchange resin (Amberlite CG50) (2.4 g) was added, the mixture was allowed to stand for 30 minutes. The platinum black and Amberlite CG50 in the reaction mixture were filtered out through Celite 545, which was washed with distilled water/dioxane (1:1). The filtrate was concentrated under reduced pressure to about ⅔ volume. Then, silica gel (Lichroprep Si60) (2.052 g) was added and the mixture was further concentrated to a solid. As the residue, brown powder (3.071 g) composed of the reaction product covering the Lichroprep Si60 was obtained. The powder was put on the top of a column and purified by a dry packed column [Lichroprep Si60 (150 g), chloroform/methanol/water (75:26:5)] to obtain a yellow solid (0.463 g). The solid was dissolved in dioxane (46 ml) and distilled water (9 ml), the insolubles were filtered out and discarded. The filtrate was further dissolved in hot water and filtered while heated. The filtrate was concentrated under reduced pressure to obtain a light yellow solid (0.418 g). The solid was recrystallized from water to obtain the above-captioned compound (0.305 g, yield=33.8%) as light yellow granular crystals.

Melting point: 190°–195° C. (decomposition)

Rf: 0.37 (chloroform/methanol/water (7:3:0.5))

Mass spectrum (m/e, FAB): 489 (M+2Na)

$^1$H-NMR (DMSO-d6, δ ppm): 3.28 (m, 3H, C2, C3, C4), 3.54 (d, 1H, C5), 5.01 (d, 1H, C1), 5.27 (s, 2H, —CH$_2$O), 6.29 (d, 1H, coumarin), 7.14 (s, 1H, coumarin), 7.33 (t, 1H, phenyl), 7.40 (t, 2H, phenyl), 7.42 (s, 1H, coumarin), 7.52 (d, 2H, phenyl), 7.89 (d, 1H, coumarin)

IR spectrum (KBr, ν cm$^{-1}$): 3430s, 1715s, 1615m, 1560m, 1520m, 1435m, 1395m, 1380m, 1280s, 1245m

Example 22

Preparation of 6-α-(β-glucopyranosideuronate)-7-hydroxycoumarin [Ib-7] (step 9 wherein a sugar component is glucuronic acid)

Methanol/distilled water (4:6) (30 ml) was added to 6-D-(β-glucopyranosideuronate)-7-benzyloxycoumarin [IIb-7] (1.504 g) prepared in Example 21 and 10% Pd/C (0.15 g), and the mixture was stirred at room temperature for 3 hours. After the completion of the reaction was confirmed by TLC, the Pd/C was filtered out through G4 glass filter. The filtrate was concentrated under reduced pressure, washed with ether and chloroform and dried to obtain the above-captioned compound (1.162 g, yield=96.9%) as a yellow solid.

Melting point: 198° C. (decomposition)

Rf: 0.20 (chloroform/methanol/water (7:3:0.5))

Mass spectrum (m/e, FAB): 355 (M+1)

$^1$H-NMR (D$_2$O, δ ppm): 3.70 (m, 3H, C2, C3, C4), 3.96 (d, 1H, C5), 5.14 (1H, C1), 6.30 (d, 1H, coumarin), 6.87 (s, 1H, coumarin), 7.33 (s, 1H, coumarin), 7.89 (d, 1H, coumarin), IR spectrum (KBr, ν cm$^{-1}$): 3400s, 1690s, 1610s, 1560s, 1510w, 1395m, 1295m, 1260m

Example 23

Preparation of 6-(β-2-acetoamide-2-deoxy-6-O-pivaloyl-D-glucopyranosyloxy)-7-benzyloxyqoumarin [IIb-2p] (introduction of one acyl group wherein a sugar component is glucosamine)

In anhydrous pyridine (200 ml), 6-(β-2-acetoamide-2-deoxy-D-glucopyranosyloxy)-7-benzyloxycoumarin [IIb-2] (10.0 g) prepared in Example 12 was suspended. To the suspension, pivalic anhydride (4.74 g) and 4-dimethylaminopyridine (2.59 g) were added, and the mixture was stirred at room temperature for 3 days. After the reaction was completed, the solvent was evaporated under reduced pressure. The residue was purified by silica gel column chromatography [Kieselgel 60 (500 g), chloroform/methanol (15:1)] to obtain the above-captioned compound (9.11 g, yield=77%) as a white solid.

Melting point: 179.5°–182.0° C.

Mass spectrum (m/e, FAB): 556 (M+1)

$^1$H-NMR (CDCl$_3$, 500MHz, δ ppm): 1.06 (s, 9H, tBu), 1.76 (s, 3H, CH$_3$CO—), 3.24 (td, 1H, H-4'), 3.48 (br q, 1H, H-3'), 3.57–3.61 (m, 1H, H-5'), 3.72 (q, 1H, H-2'), 4.05 (dd, 1H, H-6'a), 4.36 (d, 1H, H-6'b), 5.12 (d, 1H, H-1'), 5.18 (d, 1H, 3'-OH), 5.24 (d, 1H, PhCH$_2$—), 5.27 (d, 1H, PhCH$_2$—), 5.38 (d, 1H, 4'-OH), 6.31 (d, 1H, H-4), 7.18 (s, 1H, H-5)

IR spectrum (KBr disk, ν cm$^{-1}$): 3400m, 1725s, 1655m, 1615m, 1275s

Example 24

Preparation of 6-(β-2-acetoamide-2-deoxy-6-O-pivaloyl-D-glucopyranosyloxy)-7-hydroxycoumarin [Ib-2P] (step similar to step 9 wherein a sugar component is glucosamine)

10% Pd/C (30 mg) was added to a solution of 6-(β-2-acetoamide-2-deoxy-6-O-pivaloyl-D-glucopyranosyloxy)-

7-benzyloxycoumarin [IIb-2P] (532 mg) prepared in Example 23 in dimethoxyethylene (16 ml). The mixture was stirred in a hydrogen atmosphere at room temperature for 3 hours. After the reaction was completed, the catalyst was removed by filtration. The solvent was evaporated under reduced pressure to obtain a light yellow solid (443 mg). The solid was recrystallized from hot water to obtain the above-captioned compound (358 mg, yield=77%) as white needle crystals.

Melting point: 133.0°–136.0° C.

Mass spectrum (m/e, FAB): 466 (M$^+$+1)

$^1$H-NMR (DMSO-d6, 500MHz, δ ppm): 1.06 (s, 9H, tBu), 1.84 (s, 3H, CH$_3$CO—), 3.23 (td, 1H, H-4'), 3.53 (br q, 1H, H-3'), 3.57–3.61 (m, 1H, H-5'), 3.62 (q, 1H, H-2'), 4.04 (dd, 1H, H-6'a), 4.39 (d, 1H, H-6'b), 5.07 (d, 1H, H-1'), 5.19 (d, 1H, 3'-OH), 5.38 (d, 1H, 4'-OH), 6.24 (d, 1H, H-4), 6.81 (s, 1H, H-5), 7.28 (s, 1H, H-8), 7.90 (d, 1H, H-3), 7.94 (d, 1H, —NHCOCH$_3$), 9.91 (br s, 1H, ArOH)

IR spectrum (KBr disk, ν cm$^{-1}$): 3400s, 1720s, 1650s, 1620s, 1565s, 1300s, 1280s, 1255s, 1170m, 1140m, 1070s

Example 25

Preparation of 6-(β-2-acetoamide-2-deoxy-4,6-O-benzylidene-D-glucopyranosyloxy)-7-benzyloxycoumarin [IIb-2B] (introduction of benzylidene group wherein a sugar component is glucosamine)

To a solution of 6-(β-2-acetoamide-2-deoxy-D-glucopyranosyloxy)-7-benzyloxycoumarin [IIb-2] (471.5 mg) prepared in Example 12 in dimethylformamide (10 ml) were added p-toluenesulfonic acid (5.7 mg) and benzaldehyde dimethylacetal (761 mg). The mixture was stirred at room temperature overnight. Because some starting material remained, further benzaldehyde dimethylacetal (761 mg) was added and the mixture was further stirred at room temperature overnight. The reaction solution was poured in distilled water, and the precipitated crystal was filtered out. Then, the crystals were washed with distilled water and ether, dried, and recrystallized from dioxane to obtain the above-captioned compound (0.4402 g, yield=78.7%).

Melting point: 251°–253° C.

Rf: 0.66 (chloroform/methanol (8:1))

Mass spectrum (m/e, FAB): 560 (M$^+$)

$^1$H-NMR (DMSO-d6, δ ppm): 1.77 (s, 3H), 3.58 (m, 2H), 3.76 (m, 2H), 3.85 (q, 1H), 4.25 (dd, 1H), 5.24 (m, 3H), 5.45 (d, 1H), 5.64 (s, 1H), 6.32 (d, 1H), 7.14 (s, 1H), 7.33 (t, 1H), 7.39 (m, 5H), 7.46 (m, 5H), 7.91 (d, 1H), 7.97 (dd, 1H)

IR spectrum (KBr, ν cm$^{-1}$): 3440m, 3250m, 3070m, 2860m, 1720s, 1650s, 1610s, 1550s, 1515s, 1445m, 1430m, 1370s, 1605m, 1275s, 1240s, 1195m, 1165m, 1140s, 1080s, 1020s

Example 26

Preparation of 6-(β-2-acetoamide-2-deoxy-4,6-O-benzylidene-D-glucopyranosyloxy)-7-hydroxycoumarin [Ib-2B] (step similar to step 9 wherein a sugar component is glucosamine)

10% Pd/C (36.4 mg) was added to a solution of 6-(β-2-acetoamide-2-deoxy-4,6-O-benzylidene-D-glucopyranosyloxy)-7-benzyloxycoumarin [IIb-2B] (727 mg) prepared in Example 25 in dioxane (80 ml). The mixture was stirred under a hydrogen gas stream at room temperature overnight. The reaction solution was filtered through celite to remove the Pd/C and the filtrate was concentrated under reduced pressure to obtain crystals (567.3 mg). The crystals were recrystallized from dioxane to obtain the above-captioned compound (0.2696 g, yield=44.2%).

Melting point: 250°–251° C. (decomposition)

Rf: 0.52 (chloroform/methanol (8:1))

Mass spectrum (m/e, FAB): 470 (M$^+$)

$^1$H-NMR (DMSO-d6, δ ppm): 1.83 (s, 3H), 3.56 (t, 2H), 3.76 (m, 3H), 4.26 (m, 1H), 5.18 (d, 1H), 5.44 (d, 1H), 5.64 (s, 1H), 6.24 (d, 1H), 6.81 (s, 1H), 7.38 (m, 4H), 7.46 (m, 2H), 7.92 (d, 1H), 8.02 (d, 1H), 9.96 (s, 1H)

IR spectrum (KBr, ν cm$^{-1}$): 3370m, 3060m, 2890m, 1720s, 1705s, 1655s, 1610s, 1560s, 1515m, 1440m, 1690m, 1370m, 1300s, 1270m, 1255s, 1210m, 1170m, 1140m, 1085s, 1025s

Example 27

Acute toxicity of esculetin derivatives

The acute toxicity of the present substance was examined using Crj: CD-1 (ICR) male mice (6 weeks old) and Wistar male rats (6 weeks old). 6-(β-2-acetoamide-2-deoxy-D-glucopyranosyloxy)-7-hydroxycoumarin [Ib-2] (Example 13) was administered orally at doses of 1000 and 2000 mg/kg and the conditions of animals were observed for seven days. No deaths were observed. Further, no change was observed compared with the control group in either the general state and body weight. Similar results are observed for other compounds as follows, that is, 6-(β-2,3,4,6-tetra-O-acetyl-D-galactosyloxy)-7-benzyloxycoumarin [IIa-1], 6-(β-2,3,4,6-tetra-O-acetyl-D-galactosyloxy)-7-hydroxylcoumarin [Ia-1], 6-α-D-galactosyloxy-7-benzyloxycoumarin [IIb-1], 6-α-D-galactosyloxy-7-hydroxycoumarin [Ib-1], 6-(β-2-acetoamide-3,4,6-tri-O-acetyl-2-deoxy-D-glucopyranosyloxy)-7-benzyloxycoumarin [IIa-2], 6-(β-2-acetoamide-3,4,6-tri-O-acetyl-2-deoxy-D-glucopyranosyloxy)-7-hydroxycoumarin [Ia-2], 6-(β-2-acetoamide-2-deoxy-D-glucopyranosyloxy)-7-benzyloxycoumarin [IIb-2], 6,7-bis(β-2-acetoamido-3,4,6-tri-O-acetyl-2-deoxy-α-D-glucopyranosyloxy) coumarin [Ia-6], 7-benzyloxy-6-(β-2-acetoamide-3,4,6-tri-O-acetyl-2-deoxy-D-glucopyranosyloxy)-4-methylcoumarin [IIa-12], 7-benzyloxy-6-(β-2-acetoamide-2-deoxy-D-glucopyranosyloxy)-4-methylcoumarin [IIb-12], 7-hydroxyl-6-(β-2-acetoamide-2-deoxy-D-glucopyranosyloxy)-4-methylcoumarin [Ib-12], 6-(β-2-amino-2-deoxy-D-glucopyranosyloxy)-7-benzyloxycoumarin hydrochloride [IIb-2'], 6-(β-2-amino-2-deoxy-D-glucopyranosyloxy)-7-hydroxycoumarin hydrochloride [Ib-2'], 6-α-(β-glucopyranosideuronate)-7-benzyloxycoumarin [IIb-7], 6-α-(β-glucopyranosideuronate)-7-hydroxycoumarin [Ib-7], 6-(β-2-acetoamide-2-deoxy-6-O-pivaloyl-D-glucopyranosyloxy)-7-benzyloxycoumarin [IIb-2P], 6-(β-2-acetoamide-2-deoxy-6-O-pivaloyl-D-glucopyranosyloxy)-7-hydroxycoumarin [Ib-2P], 6-(β-2-acetoamide-2-deoxy-4,6-O-benzylidene-D-glucopyranosyloxy)-7-benzyloxycoumarin [IIb-2B], 6-(β-2-acetoamide-2-deoxy-4,6-O-benzylidene-D-glucopyranosyloxy)-7-hydroxycoumarin [Ib-2B]. In the experiments, two animals were used for each group.

Example 28

Pharmacokinetic analysis and inhibitory effect on proteoglycan (PG) loss in mouse FHC model (1) Preparation of model mice The model mice were prepared in accordance with the method described in D. A. Willoughby et al., Agents Actions, vol. 38, pp. 126 to 134, 1993.

The left and right femoral head cartilages (FHC) of S.D. male rats were excised sterilely in a clean bench. The excised FHC's were washed with a Ham F-12 culture medium containing antibiotics and the wet weight was measured. Then the FHC's were wrapped in two cotton sheets (about 1 cm×1 cm) and cooled with ice in the culture medium until implantation. The FHC's were implanted sterilely under the dorsal skin of BALB/C female mice whose dorsal regions were shaved. The incisions were stitched, and then completely sealed with surgical adhesive.
(2) Pharmacokinetic analysis in FHC after administering esculetin and 6-(β-2-acetoamide-2-deoxy-D-glucopyranosyloxy)-7-hydroxycoumarin [Ib-2]

The above mouse FHC model were used to compare the kinetics of esculetin and present substance [Ib-2]. 10 mg/kg of esculetin and an equimolar amount, i.e., 21 mg/kg, of the present substance [Ib-2] were administered under the dorsal skin (around FHC) three days after the implantation of the FHC. The FHC's were periodically removed and digested with papain. Then, an amount of the compounds taken up in the FHC was analyzed by high performance liquid chromatography. In the above experiments, five mice were used for each group.

The results are shown in FIG. 1. The amounts of the present substance [Ib-2] incorporated in FHC following administration of [Ib-2] are shown by the open circles (o) in FIG. 1 and the amounts of esculetin incorporated in FHC following administration of esculetin are shown by the closed circles (•). As shown in FIG. 1, the present substance [Ib-2] is incorporated and retained in the FHC in a higher concentration as compared to the administration of esculetin.

(3) Inhibitory effect of present substance [Ib-2] on proteoglycan (PG) loss.

The above mouse FHC model were used to examine the inhibitory effect of the present substance [Ib-2] on PG loss using mouse FHC model. The present substance [Ib-2] was orally administered at the dose of 400 mg/kg for 11 days once a day starting from the 7th day after implantation of the FHC. After the administration was completed, the FHC's were removed and digested with papain. Then, the amount of glycosaminoglycan (GAG) in the FHC was measured as an indication of proteoglycan content using the method described by R. W. Farndale et al., Connective Tissue Research, vol. 9, pp. 247 to 248, 1982. In the above experiment, six mice were used for each group.

Figure 2:
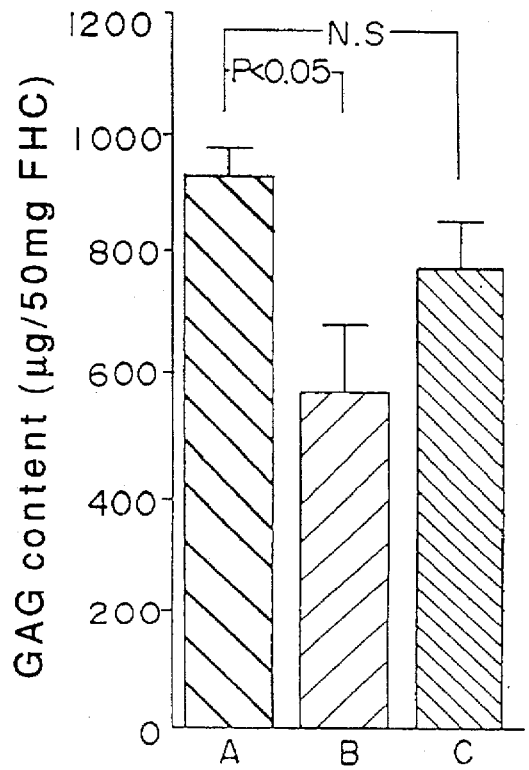
FIG. 2 is a graph showing the action to suppress the reduction of proteoglycan by the compound of the present invention in the FHC of the mouse FHC model, as disclosed in Example 28(3).

FIG. 2 shows the amount of GAG contained in 50 mg of FHC in each group. As shown in FIG. 2, the control group (B in FIG. 2) exhibited a significant reduction of the amount of GAG in the FHC in comparison with the start of the administration (seven days after implantation of FHC) (A in FIG. 2), whereas the group to which the present substance [Ib-2] was administered (C in FIG. 2) exhibited an action to inhibit the proteoglycan loss.

As clearly shown, the novel esculetin derivatives of the present invention strongly suppress the reduction of the proteoglycan in the cartilage matrix and thereby exhibits a chondroprotective action. For the amount of incorporation; affinity and local retention in the cartilage matrix, the novel esculetin derivatives of the present invention is superior to esculetin, 4-alkylesculetin or the like. Further, the novel esculetin derivatives of the present invention show low toxicity. Accordingly, the esculetin derivatives of the present invention are extremely useful as an active ingredient in pharmaceutical compositions, particularly chondroprotective agents, or for the treatment of arthropathy, such as rheumatoid arthritis, osteoarthritis, periarthritis humeroscapularis, shoulder-arm-neck syndrome, lumbago, and so on.

Although the present invention has been described with reference to specific embodiments, various changes and modifications obvious to those skilled in the art are deemed to be within the spirit, scope, and concept of the invention.

We claim:
1. A compound of the formula (I):

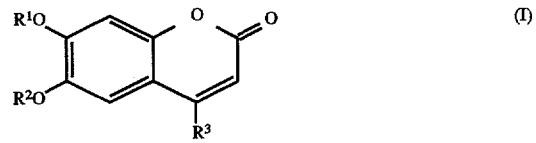

wherein $R^1$ and $R^2$ are, independently,
  i) a hydrogen atom,
  ii) a monosaccharide residue,
  iii) a protected monosaccharide residue, or
  iv) a protecting group for hydroxyl group,
but at least one of $R^1$ and $R^2$ is a monosaccharide residue or a protected monosaccharide residue, and $R^3$ is
  i) a hydrogen atom,
  ii) a hydroxyl group,
  iii) an alkyl group having 1–4 carbon atoms,
  iv) an aryl group having 6–12 carbon atoms, or
  v) an aralkyl group consisting of an alkyl group having 1–4 carbon atoms substituted with an aryl group having 6–12 carbon atoms,
with the proviso that
  1) when $R^1$ and $R^2$ are glucose residues at the same time, $R^3$ is not a hydrogen atom,
  2) when $R^1$ is a hydrogen atom or a benzyl group and $R^2$ is a glucose residue, an acetylated glucose residue, or acetalized glucose residue, $R^3$ is not a hydrogen atom, or
  3) when $R^1$ is a glucose residue and $R^2$ is a hydrogen atom, $R^3$ is not a hydrogen atom, or
  4) when $R^2$ is a glucose residue, $R^3$ is not a hydrogen atom,
or a pharmaceutically acceptable salt thereof.

2. A compound according to claim 1, wherein $R^3$ is a hydrogen atom, a hydroxyl group, an alkyl group having 1–4 carbon atoms, or phenyl group or a pharmaceutically acceptable salt thereof.

3. A compound according to claim 1, wherein the monosaccharide residue is a protected monosaccharide residue in which 1 to all hydroxyl groups are acylated, sulfonated or phosphated, or 2 or 4 hydroxyl groups are acetalized.

4. A method for manufacturing a compound of the formula (XV):

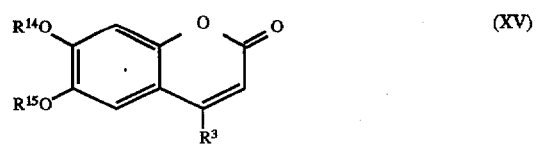

wherein $R^{14}$ and $R^{15}$ are independently,
  i) a protected monosaccharide residue, or
  ii) a protecting group for hydroxyl group,
but at least one of $R^{14}$ and $R^{15}$ is a protected monosaccharide residue, and $R^3$ is
  i) a hydrogen atom,
  ii) a hydroxyl group,
  iii) an alkyl group having 1–4 carbon atoms iv) an aryl group having 6–12 carbon atoms, or v) an aralkyl group consisting of an alkyl group having 1–4 carbon atoms substituted with an aryl group having 6–12 carbon atoms, comprising reacting, in the presence of a phase transfer catalyst, a compound of the formula (XVI):

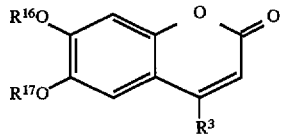

(XVI)

wherein $R^{16}$ and $R^{17}$ are independently i) a hydrogen atom, ii) a protected monosaccharide residue, or iii) a protecting group for hydroxyl group, but at least one $R^{16}$ and $R^{17}$ is a hydrogen atom, and $R^3$ has the same meaning as above, and a compound of the formula (IV)

$$R^5\text{—X} \quad \text{(IV)}$$

wherein $R^4$ is a protected monosaccharide residue and X is a halogen atom.

5. A method for manufacturing a compound of the formula (XIII):

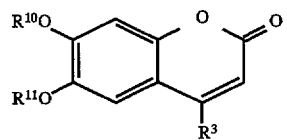

(XIII)

wherein one of $R^{10}$ and $R^{11}$ is, i) a monosaccharide residue, or ii) a protected monosaccharide residue, and the other is a hydrogen atom, and $R^3$ is i) a hydrogen atom, ii) alkyl group having 1–4 carbon atoms, iii) aryl group having 6–12 carbon atoms, iv) aralkyl group consisting of an alkyl group having 1–4 carbon atoms, substituted with an aryl group having 6–12 carbon atoms, or v) a hydroxyl group, with the proviso that 1) when $R^{10}$ is a hydrogen atom and $R^{11}$ is a glucose residue, an acetylated glucose residue, or acetalized glucose residue, $R^3$ is not a hydrogen atom, 2) when $R^{10}$ is a glucose residue and $R^3$ is a hydrogen atom, $R^3$ is not a hydrogen atom, or 3) when $R^{11}$ is a glucose residue, $R^3$ is not a hydrogen atom, comprising hydrogenolyzing a compound of the formula (XIV):

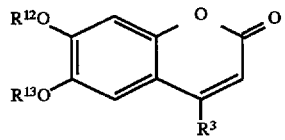

(XIV)

wherein one of $R^{12}$ and $R^{13}$ is a monosaccharide residue or a protected monosaccharide residue and the other is a protecting group for hydroxyl group, and $R^3$ has the same meaning as above.

6. A method for manufacturing a compound of the formula (XI):

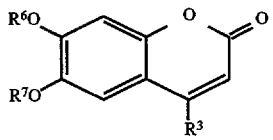

(XI)

wherein $R^6$ and $R^7$ are independently i) a hydrogen atom, ii) a monosaccharide residue, or iii) a protecting group for hydroxyl group, but at least one of $R^6$ and $R^7$ is a monosaccharide residue and $R^3$ is i) a hydrogen atom, ii) a hydroxyl group, iii) alkyl group having 1–4 carbon atoms, iv) aryl group having 6–12 carbon atoms, v) aralkyl group consisting of an alkyl group having 1–4 carbon atoms substituted with an aryl group having 6–12 carbon atoms, with the proviso that 1) when $R^6$ and $R^7$ are glucose residues at the same time, $R^3$ is not a hydrogen atom, 2) when $R^6$ is a hydrogen atom or a benzyl group and $R^7$ is a glucose residue, $R^7$ is a glucose residue, $R^3$ is not a hydrogen atom, or 3) when $R^6$ is a glucose residue and $R^7$ is a hydrogen atom, $R^3$ is not a hydrogen atom, comprising removing, in an organic solvent, in the presence of an alkali metal dissolved in an alcohol, one or more protecting groups in a protected monosaccharide residue in a compound of the formula (XII):

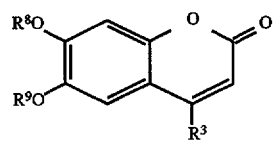

(XII)

wherein one of $R^8$ and $R^9$ are independently i) a hydrogen atom, ii) a protected monosaccharide residue, or iii) a protecting group for hydroxyl group, but at least one of $R^8$ and $R^9$ is a protected monosaccharide residue, and $R^3$ has the same meaning as above.

7. A pharmaceutical composition comprising chondroprotective amounts of a compound of the formula (I):

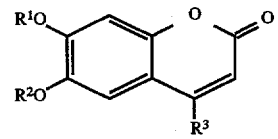

(I)

wherein $R^1$ and $R^2$ are, independently, i) a hydrogen atom, ii) a monosaccharide residue, iii) a protected monosaccharide residue, or iv) a protecting group for hydroxyl group, but at least one of $R^1$ and $R^2$ is a monosaccharide residue or a protected monosaccharide residue, and $R^3$ is i) a hydrogen atom, ii) a hydroxyl group, iii) an alkyl group having 1–4 carbon atoms, iv) an aryl group having 6–12 carbon atoms, v) an aralkyl group consisting of an alkyl group having 1–4 carbon atoms substituted with an aryl group having 6–12 carbon atoms, with the proviso that 1) when $R^1$ and $R^2$ are glucose residues at the same time, is not a hydrogen atom, 2) when $R^1$ is a hydrogen atom or a benzyl group and $R^2$ is a glucose residue, an acetylated glucose residue, or acetalized glucose residue, $R^3$ is not a hydrogen atom, or 3) when $R^1$ is a glucose residue and $R^2$ is a hydrogen atom, $R^3$ is not a hydrogen atom, or 4) when $R^2$ is a glucose residue, $R^3$ is not a hydrogen atom, or a pharmaceutically acceptable salt thereof, and a pharmaceutically acceptable carrier.

8. A method for treating arthropathy, in mammals, comprising administering a chondroprotective amount of a compound of the formula (I):

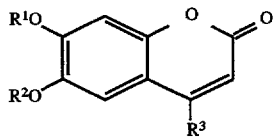

wherein $R^1$ and $R^2$ are, independently, i) a hydrogen atom, ii) a monosaccharide residue, iii) a protected monosaccharide residue, or iv) a protecting group for hydroxyl group, but at least one of $R^1$ and $R^2$ is a monosaccharide residue or a protected monosaccharide residue, and $R^3$ is i) a hydrogen atom, ii) a hydroxyl group, iii) an alkyl group having 1–4 carbon atoms, iv) an aryl group having 6–12 carbon atoms, v) an aralkyl group consisting of an alkyl group having 1–4 carbon atoms substituted with an aryl group having 6–12 carbon atoms, with the proviso that 1) when $R^1$ and $R^2$ are glucose residues at the same time, $R^3$ is not a hydrogen atom, 2) when $R^1$ is a hydrogen atom or a benzyl group and $R^2$ is a glucose residue, an acetylated glucose residue, or acetalized glucose residue, $R^3$ is not a hydrogen atom, or 3) when $R^1$ is a glucose residue and $R^2$ is a hydrogen atom, $R^3$ is not a hydrogen atom, or a pharmaceutically acceptable salt thereof, said arthropathy being rheumatoid arthritis, osteoarthritis, periarthritis, humeroscapularis, shoulder-arm-neck syndrome, or lumbago.

* * * * *

UNITED STATES PATENT AND TRADEMARK OFFICE
CERTIFICATE OF CORRECTION

Page 1 of 3

PATENT NO. : 5,736,522
DATED : April 7, 1998
INVENTOR(S) : Koju WATANABE, et al.

It is certified that error appears in the above-identified patent and that said Letters Patent is hereby corrected as shown below:

Column 11, line 58, change "acetoamide" to --acetamido--.
Column 12, line 55, change "acetoamide" to --acetamido--;
    line 58, change "acetoamide" to --acetamido--.
Column 13, line 25, change "acetoamide" to --acetamido--;
    line 28, change "acetoamide" to --acetamido--;
    line 66, change "acetoamide" to --acetamido--.
Column 14, line 24, change "acetoamide" to --acetamido--.
Column 17, line 45, change "acetoamide" to --acetamido--;
    line 47, change "acetoamide" to --acetamido--.
Column 21, line 63, change "acetoamide" to --acetamido--.
Column 22, line 26, change "acetoamide" to --acetamido--;
    line 33, change "acetoamide" to --acetamido--;
    line 61, change "acetoamide" to --acetamido--.
Column 23, line 14, change "acetoamide" to --acetamido--;
    line 52, change "acetoamide" to --acetamido--;
    line 56, change "acetoamide" to --acetamido--.
Column 24, line 21, change "acetoamide" to --acetamido--;
    line 24, change "acetoamide" to --acetamido--;
    line 55, change "acetoamide" to --acetamido--;
    line 59, change "acetoamide" to --acetamido--.
Column 25, line 23, change "acetoamide" to --acetamido--;
    line 27, change "acetoamide" to --acetamido--;
    line 30, change "acetoamide" to --acetamido--.
Column 26, line 49, change "acetoamide" to --acetamido--;
    line 54, change "acetoamide" to --acetamido--.
Column 27, line 17, change "acetoamide" to --acetamido--;
    22, change "acetoamide" to --acetamido--.
    line 53, change "acetoamide" to --acetamido--.

UNITED STATES PATENT AND TRADEMARK OFFICE
CERTIFICATE OF CORRECTION

PATENT NO. : 5,736,522
DATED : April 7, 1998
INVENTOR(S) : Koju WATANABE,

It is certified that error appears in the above-identified patent and that said Letters Patent is hereby corrected as shown below:

Column 28, line 18, change "acetoamide" to --acetamido--;
    line 21, change "acetoamide" to --acetamido--.
Column 30, line 34, change "acetoamide" to --acetamido--;
    line 39, change "acetoamide" to --acetamido--;
    line 61, change "acetoamide" to --acetamido--;
    line 66, change "acetoamide" to --acetamido--.
Column 31, line 23, change "acetoamide" to --acetamido--;
    line 27, change "acetoamide" to --acetamido--:

Column 31, line 53, change "acetoamide" to --acetamido--;
    line 59, change "acetoamide" to --acetamido--.
Column 32, line 19, change "acetoamide" to --acetamido--;
    line 31, change "acetoamide" to --acetamido--;
    line 33, change "acetoamide" to --acetamido--;
    line 35, change "acetoamide" to --acetamido--;
    line 36, change "acetoamido" to --acetamido--;
    line 38, change "acetoamide" to --acetamido--;
    line 40, change "acetoamide" to --acetamido--;
    line 42, change "acetoamide" to --acetamido--;
    line 50, change "acetoamide" to --acetamido--;
    line 51, change "acetoamide" to --acetamido--;
    line 53, change "acetoamide" to --acetamido--;
    line 55, change "acetoamide" to --acetamido--.
Column 33, line 11, change "acetoamide" to --acetamido--.

Column 34, line 46, after "the" insert --protected--;
    line 47, delete "protected.

UNITED STATES PATENT AND TRADEMARK OFFICE
CERTIFICATE OF CORRECTION

PATENT NO. : 5,736,522
DATED : April 7, 1998
INVENTOR(S) : Koju Watanabe, et al.

It is certified that error appears in the above-identified patent and that said Letters Patent is hereby corrected as shown below:

Column 35, line 24, replace "$R^4$" with --$R^5$--;
        line 51, replace "$R^3$" with --$R^{11}$--;
        line 53, after "a" insert     --[6'-O-β-hydroxy-3-methylglutaryl)]--.
Column 36, line 28, replace "iS" with --is-- and delete "$R^7$ is a glucose residue,"
Column 37, line 8, before "is" insert --$R^3$--;
        line 15, after "a" (first occurrence) insert --[6'-O-β-hydroxy-3-methylglutaryl)]--.

Signed and Sealed this

First Day of December, 1998

Attest:

BRUCE LEHMAN

Attesting Officer      Commissioner of Patents and Trademarks